United States Patent
Shen et al.

(10) Patent No.: US 8,324,450 B2
(45) Date of Patent: Dec. 4, 2012

(54) NON-HUMAN ANIMAL MODEL FOR FRONTOTEMPORAL LOBAR DEGENERATION WITH UBIQUITIN-POSITIVE INCLUSIONS (FTLD-U)

(75) Inventors: Che-Kun James Shen, Taipei (TW); Kuen-Jer Tsai, Kaohsiung (TW)

(73) Assignee: Academia Sinica, Taipei (TW)

( * ) Notice: Subject to any disclaimer, the term of this patent is extended or adjusted under 35 U.S.C. 154(b) by 292 days.

(21) Appl. No.: 12/785,653

(22) Filed: May 24, 2010

(65) Prior Publication Data

US 2010/0306862 A1     Dec. 2, 2010

Related U.S. Application Data

(60) Provisional application No. 61/183,327, filed on Jun. 2, 2009.

(51) Int. Cl.
  *G01N 33/68*  (2006.01)
  *A01K 67/027*  (2006.01)
  *C12N 5/079*  (2010.01)

(52) U.S. Cl. ................ 800/18; 800/3; 435/354

(58) Field of Classification Search ............ None
See application file for complete search history.

(56) References Cited

FOREIGN PATENT DOCUMENTS

WO     2009/125846 A1     10/2009

OTHER PUBLICATIONS

Xu et al (The Journal of Neurosicence, 2010; 30(32): 10851-10859).*
Xu et al (Generation and characterization of human TDP-43 transgenic mice. Program# 638.2/ Poster# K3. 2008 Neuroscience Meeting Planner. Society for Neuroscience. online).*
Wegorzewska et al. (PNAS. Nov 2009; 106(44): 18809-18814).*
Wils et al. (PNAS Feb. 2010; 107(8): 3858-3863).*
Mayford et at., "The 3'-untranslated region of CaMkIIα is a cis-acting signal for the localization and translation of mRNA indendrites" Proc. Natl. Acad. Sci. USA vol. 93, pp. 13250-13255, Nov. 1996.
Wegorzewskaa et al., "TDP-43 mutant transgenic mice develop features of ALS and frontotemporal lobar degeneration" Proc. Natl. Acad. Sci. USA vol. 106, pp. 18809-18814, Nov. 2009.
Wits, et al., "TDP-43 transgenic mice develop spastic paralysis and neuronal inclusions characteristic of ALS and frontotemporal lobar degeneration" vol. 107, pp. 3858-3863, Feb. 2010.
Verbeeck et al: "p1-052: Somatic brain transgenic TDP-43 mice" Alzheimer's & Dementia: The Journal of the Alzheimer's association, Elsevier, New York, NY, US, vol. 4, No. 4, Jul. 1, 2008, p. T221.
Neumann M: "TDP-43 proteinopathies: A new class of proteinopathies" Future Neurology, Future medicine, vol. 2, No. 5, Jan. 1, 2007, pp. 549-557.
Wang et al. "TDP-43: an emerging new player in neurodegenerative diseases" Trends in Molecular Medicine, Elsevier Current Trends, J. Molmed. Vo. 14, No. 11, Nov. 1, 2008, pp. 479-485.
Nonaka et al. "Phosphorylated and ubiquitinated TDP-43 pathological inclusions in ALS and FTLD-U are recapitulated in SH-SY5Y cells" FEBS Letters, Elsevier Amsterdam, vol. 583, No. 2, Jan. 22, 2009, pp. 394-400.
European Search Report for the EU counterpart application.

* cited by examiner

*Primary Examiner* — Scott Long
(74) *Attorney, Agent, or Firm* — Hsiu-Ming Saunders; Intellectual Property Connections, Inc.

(57) ABSTRACT

Non-human animal models for frontotemporal lobar degeneration with ubiquitin-positive inclusions (FTLD-U) are disclosed. The invention relates to a transgenic mouse whose genome comprises a transgene operably linked to a neuronal specific promoter effective for an increased expression of the transgene in the brain of the mouse, in which the transgene comprises a nucleotide sequence encoding TAR DNA-binding protein 43 (TDP-43). The transgenic mouse exhibits reduced or impaired learning and memory capacity, and may further exhibits progressively impaired or reduced motor functions. Methods of using such animal models are also disclosed.

18 Claims, 9 Drawing Sheets

SEQUENCE LISTING

```
<160> NUMBER OF SEQ ID NOS: 4

<210> SEQ ID NO 1
<211> LENGTH: 414
<212> TYPE: PRT
<213> ORGANISM: Mus musculus

<400> SEQUENCE: 1

Met Ser Glu Tyr Ile Arg Val Thr Glu Asp Glu Asn Asp Glu Pro Ile
1               5                   10                  15

Glu Ile Pro Ser Glu Asp Asp Gly Thr Val Leu Leu Ser Thr Val Thr
                20                  25                  30

Ala Gln Phe Pro Gly Ala Cys Gly Leu Arg Tyr Arg Asn Pro Val Ser
            35                  40                  45
```

```
Gln Cys Met Arg Gly Val Arg Leu Val Glu Gly Ile Leu His Ala Pro
 50                  55                  60

Asp Ala Gly Trp Gly Asn Leu Val Tyr Val Val Asn Tyr Pro Lys Asp
 65                  70                  75                  80

Asn Lys Arg Lys Met Asp Glu Thr Asp Ala Ser Ser Ala Val Lys Val
                 85                  90                  95

Lys Arg Ala Val Gln Lys Thr Ser Asp Leu Ile Val Leu Gly Leu Pro
                100                 105                 110

Trp Lys Thr Thr Glu Gln Asp Leu Lys Asp Tyr Phe Ser Thr Phe Gly
            115                 120                 125

Glu Val Leu Met Val Gln Val Lys Lys Asp Leu Lys Thr Gly His Ser
            130                 135                 140

Lys Gly Phe Gly Phe Val Arg Phe Thr Glu Tyr Glu Thr Gln Val Lys
145                 150                 155                 160

Val Met Ser Gln Arg His Met Ile Asp Gly Arg Trp Cys Asp Cys Lys
                165                 170                 175

Leu Pro Asn Ser Lys Gln Ser Pro Asp Glu Pro Leu Arg Ser Arg Lys
                180                 185                 190

Val Phe Val Gly Arg Cys Thr Glu Asp Met Thr Ala Glu Glu Leu Gln
                195                 200                 205

Gln Phe Phe Cys Gln Tyr Gly Glu Val Val Asp Val Phe Ile Pro Lys
210                 215                 220

Pro Phe Arg Ala Phe Ala Phe Val Thr Phe Ala Asp Asp Lys Val Ala
225                 230                 235                 240

Gln Ser Leu Cys Gly Glu Asp Leu Ile Ile Lys Gly Ile Ser Val His
                245                 250                 255

Ile Ser Asn Ala Glu Pro Lys His Asn Ser Asn Arg Gln Leu Glu Arg
                260                 265                 270

Ser Gly Arg Phe Gly Gly Asn Pro Gly Gly Phe Gly Asn Gln Gly Gly
            275                 280                 285

Phe Gly Asn Ser Arg Gly Gly Ala Gly Leu Gly Asn Asn Gln Gly
            290                 295                 300

Gly Asn Met Gly Gly Gly Met Asn Phe Gly Ala Phe Ser Ile Asn Pro
305                 310                 315                 320

Ala Met Met Ala Ala Ala Gln Ala Ala Leu Gln Ser Ser Trp Gly Met
                325                 330                 335

Met Gly Met Leu Ala Ser Gln Gln Asn Gln Ser Gly Pro Ser Gly Asn
            340                 345                 350

Asn Gln Ser Gln Gly Ser Met Gln Arg Glu Pro Asn Gln Ala Phe Gly
            355                 360                 365

Ser Gly Asn Asn Ser Tyr Ser Gly Ser Asn Ser Gly Ala Pro Leu Gly
            370                 375                 380

Trp Gly Ser Ala Ser Asn Ala Gly Ser Gly Ser Gly Phe Asn Gly Gly
385                 390                 395                 400

Phe Gly Ser Ser Met Asp Ser Lys Ser Ser Gly Trp Gly Met
                405                 410

<210> SEQ ID NO 2
<211> LENGTH: 23
<212> TYPE: DNA
<213> ORGANISM: Artificial Sequence
<220> FEATURE:
<223> OTHER INFORMATION: forward primer

<400> SEQUENCE: 2
```

```
-continued ggcttgagat ctggccatac act                                          23

<210> SEQ ID NO 3
<211> LENGTH: 26
<212> TYPE: DNA
<213> ORGANISM: Artificial Sequence
<220> FEATURE:
<223> OTHER INFORMATION: reverse primer

<400> SEQUENCE: 3
taagatcttt cttgacctga accata                                       26

<210> SEQ ID NO 4
<211> LENGTH: 36
<212> TYPE: DNA
<213> ORGANISM: Artificial Sequence
<220> FEATURE:
<223> OTHER INFORMATION: probe sequence used for in situ hybridization

<400> SEQUENCE: 4
gctctgaatg gtttgggaat gaagacatct accact                            36
```

NON-HUMAN ANIMAL MODEL FOR FRONTOTEMPORAL LOBAR DEGENERATION WITH UBIQUITIN-POSITIVE INCLUSIONS (FTLD-U)

REFERENCE TO RELATED APPLICATION

The present application claims the priority to U.S. Provisional Application Ser. No. 61/183,327, filed Jun. 2, 2009, which is herein incorporated by reference in its entirety.

FIELD OF THE INVENTION

The present invention relates generally to a transgenic animal model for neuronal degeneration, and more specifically to a transgenic animal model for frontotemporal lobar degeneration.

BACKGROUND OF THE INVENTION

TAR DNA binding protein-43 (TDP-43) is a multifunctional DNA/RNA-binding factor that has been implicated to play a role in the regulation of the neuronal plasticity. Interestingly, TDP-43 has also been identified as the major constituent of the neuronal cytoplasmic inclusions (NCIs) characteristic of a range of neurodegenerative diseases including the frontotemporal lobar degeneration with ubiquitin-positive inclusions.(FTLD-U) and amyotrophic lateral sclerosis (ALS).

Biochemical analyses have revealed that TDP-43 is promiscuously modified/processed in the affected regions of the brains and spinal cords of the FTLD-U and ALS patients, respectively. In particular, TDP-43 derived polypeptides have been detected on. Western blots of the urea-soluble extracts from the pathological samples with TDP-43(+) UBIs, which include: 1) multiple species of high molecular weight, poly-ubiquitinated TDP-43; 2) phosphorylated TDP-43 migrating at ~45 kDa; and 3) ~25 kDa and 35 kDa C-terminal fragments of TDP-43. In addition, immunohistochemistry analysis of the pathological samples from FTLD-U and ALS patients has revealed the presence of disease cells with NCIs adjacent to TDP-43-depleted nuclei. The depletion of the nuclear TDP-43 and the formation of the UBIs have been suggested to cause loss-of-function of TDP-43 and cellular toxicity, thus leading to the pathogenesis of FTLD-U as well as ALS with the TDP-43(+) UBIs.

Using a Thy-1 promoter, Wils et al. (2010) has generated transgenic mice with overexpression of human TDP-43 in the neurons of the central nervous system in addition to other cell types in which the Thy-1 promoter is active, which include the thymocytes, myoblasts, epidermal cells and keratinocytes. Both degeneration of the cortical/spinal motor neurons associated with a spastic quadriplegia reminiscent of ALS and degeneration of the nonmotor cortical and subcortical neurons characteristic of FTLD were observed in their transgenic mice. Furthermore, cellular aggregates (NCIs and NIIs) containing ubiquitinated and phosphorylated TDP-43 as well as the 25 KDa TDP-43 fragments were detected in association with the disease development and progression of these human TDP-43 overexpressing transgenic mice.

Despite the rapidly accumulating data on the molecular and cellular properties of TDP-43 in relation to the formation TDP-43(+) NCIs or UBIs, a causative role of TDP-43 in the pathogenesis of FTLD-U remains undefined.

A previously unaddressed need exists in the art to address the aforementioned deficiencies and inadequacies, especially in connection with the roles of TDP-43 in neurodegenerative diseases.

SUMMARY OF THE INVENTION

In one aspect, the invention relates to a transgenic mouse whose genome comprises a transgene operably linked to a neuronal specific promoter effective for an increased expression of the transgene in the brain of the mouse, the transgene comprising a nucleotide sequence encoding TAR DNA-binding protein 43 (TDP-43), wherein the mouse exhibits an increased expression of TDP-43 in the brain thereof.

In another aspect, the invention relates to a method for evaluating potential therapeutic effects of a compound for treating, preventing and/or inhibiting frontotemporal lobar degeneration with ubiquitin-positive inclusions (FTLD-U) in a mammal, comprising the steps of: a) administering the compound to a transgenic mouse whose genome comprises a transgene operably linked to a neuronal specific promoter effective for an increased expression of the transgene in the brain of the mouse, the transgene comprising a nucleotide sequence encoding TAR DNA-binding protein 43 (TDP-43); and b) determining the potential therapeutic effects of the compound on the transgenic mouse by identifying improvement in learning and memory behavior and/or motor function of the tansgeinc mouse.

Further in another aspect, the invention relates to a method for identifying a candidate agent for treating, preventing and/or inhibiting FTLD-U, comprising the steps of: a) measuring the level of TDP-43 expression in the aforementioned transgenic mouse; b) administering the agent to the transgenic mouse; and c) measuring the level of TDP-43 expression in the transgenic mouse; wherein a decrease in the level of TDP-43 expression after treatment with the agent identifies the agent as a candidate agent for treating, preventing and/or inhibiting FTLD-U.

Yet in another aspect, the invention relates to a neuronal cell comprising a transgene operably linked to a neuronal specific promoter effective for an increased expression of the transgene in the neuronal cell, the transgene comprising a nucleotide sequence encoding TAR DNA-binding protein 43 (TDP-43), wherein the neuronal cell exhibits TDP-43 protein inclusion bodies in the cytosol thereof.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

DETAILED DESCRIPTION OF THE INVENTION

Definitions

Figure 1:
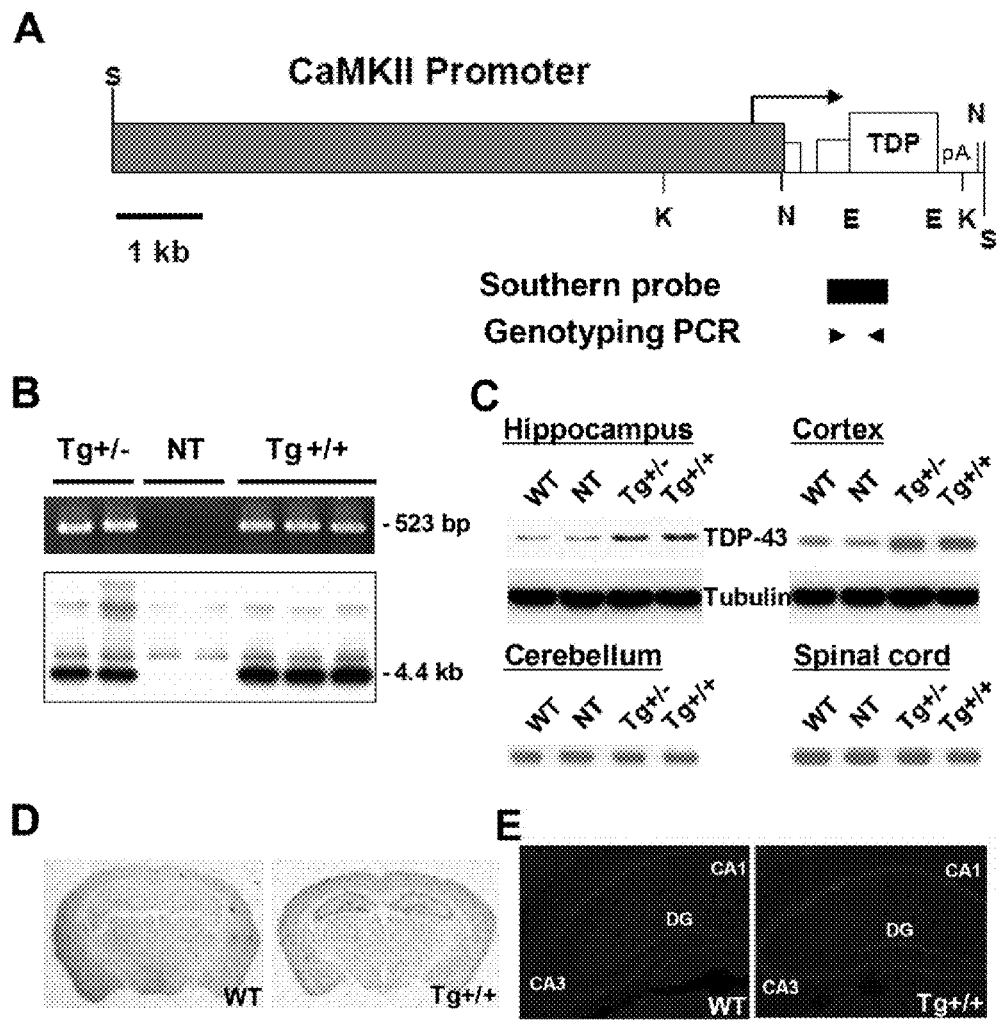
FIGS. 1A-1E show generation and characterization of CaMKII-TDP-43 Transgenic (Tg) mice.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

The term "NSE" is an abbreviation for "neuron-specific enolase (NSE)." A neuron-specific enolase (NSE) promoter is disclosed in the U.S. Pat. No. 6,649,811, U.S. Pat. No. 5,387,742; NCBI Reference Sequence: NC_000072.5; and Twyman et al., (1997) "Sequences in the proximal 5' flanking region of the rat neuron-specific enolase (NSE) gene are sufficient for cell type-specific reporter gene expression" Journal of Molecular Neuroscience, Vol. 8 (1): 63-73, all of which are herein incorporated by reference in their entireties.

The term "Hb9 promoter" refers to the motor neuron-specific Hb9 promoter, which is disclosed in the U.S. Pat. No. 7,632,679, NCBI Reference Sequence: NC_000071.5 and Lee et al., (2004) "Analysis of embryonic motoneuron gene regulation: derepression of general activators function in concert with enhancer factors" Development (131): 3295-3306, all of which are herein incorporated by reference in their entireties.

The term "DIV" means "day in vitro."

The terms "an increased expression" and "overexpression" are interchangeable. An increased expression of a tansgene shall generally mean a statistically significant increase in the amount of the expression of a tansgene as compared to a control.

The invention relates to generation of a FTLD-U mouse model with transgenic overexpression of TDP-43 in the hippocampus, cortex, and striatum with use of the CaMKII promoter. These Tg mice developed learning/memory deficits as well as impairment of their motor functions. The brains of the Tg mice were characterized with a reduce volume of the hippocampus, gliosis, and TDP-43(+), ubiquitin(+) NCIs. In interesting connection with the finding that TDP-43 expression is upregulated in some FTLD-U patients, the discovery suggests that changes in the homeostatic concentration of TDP-43, in particular the increase in its protein level, in specific types of cells could be a primary cause leading to the development of FTLD-U, and likely other neurodegenerative diseases with TDP-43(+) UBIs as well.

The invention relates to a FTLD-U mouse model (CaMKII-TDP-43 Tg) with transgenic overexpression of TDP-43 in the forebrain and phenotypic characteristics that mimic those of FTLD-U. In particular, the Tg mice exhibited impaired learning/memory, progressive motor dysfunction, and hippocampal atrophy. The cognitive and motor impairments were accompanied with reduced levels of the neuron regulators pERK and pCREB, and increased level of gliosis in the brains of the Tg mice. Moreover, cells with TDP-43(+), ubiquitin(+) NCIs and TDP-43-deleted nuclei appeared in the Tg mouse brains in an age-dependent manner. The data generated from these Tg mice provide a direct evidence that upregulated level of the TDP-43 protein in the forebrain is sufficient to lead to the formation of TDP-43(+), ubiquitin(+) NCIs and neurodegeneration. This FTLD-U mouse model is valuable for the mechanistic analysis of the role of TDP-43 in the pathogenesis of FTLD-U and for the design of effective therapeutic approaches of the disease.

In one aspect, the invention relates to a transgenic mouse whose genome comprises a transgene operably linked to a neuronal specific promoter effective for an increased expression of the transgene in the'brain of the mouse, the transgene comprising a nucleotide sequence encoding TAR DNA-binding protein 43 (TDP-43).

In one embodiment of the invention, the neuronal specific promoter is selected from the group consisting of $Ca^{2+}$/calmodulin-dependent kinaseIIα (CaMKIIα) promoter, neuron-specific enolase (NSE) promoter and motor neuron-specific gene Hb9 promoter.

In another embodiment of the invention, the neuronal specific promoter is $Ca^{2+}$/calmodulin-dependent kinaseIIα (CaMKIIα) promoter.

In another embodiment of the invention, the transgenic mouse exhibits reduced or impaired learning and memory capacity.

In another embodiment of the invention, the transgenic mouse further exhibits progressively impaired or reduced motor functions.

In another embodiment of the invention, the hippocampus and cortex, but not cerebellum and spinal cord, of the transgenic mouse exhibit an increased amount of TDP-43 protein.

The transgenic mouse may be either a homozygous or hemizygous transgenic mouse, in which the homozygous mouse and hemizygous transgenic mouse exhibit similar levels of TDP-43 protein. Alternatively, the homozygous transgenic mouse exhibits a higher level of TDP-43 transcript than the hemizygous transgenic mouse.

In another embodiment of the invention, the hippocampus and cortex, but not cerebellum and spinal cord, of the transgenic mouse exhibit at least a 2-fold increase in the level of TDP-43 protein.

In another embodiment of the invention, the hippocampus and cortex of the transgenic mouse exhibit an altered level of a protein and/or a neurotransmitter member selected from the group consisting of phosphorylated extracellular signal-regulated kinase (pERK), phosphorylated cAMP-response element-binding Protein (pCREB), glutamic acid decarboxylase 67 (GAD67), glial fibrillary acidic protein (GFAP), gamma-aminobutyric acid (GABA) and capsase-3.

In another embodiment of the invention, the brain of the transgenic mouse exhibits poly-ubiquitinated TDP-43.

Further in another embodiment of the invention, the amount of poly-ubiquitinated TDP-43 in the brain of the mouse increases with age.

Further in another embodiment of the invention, the brain neurons of the mouse exhibits cytoplasmic TDP-43 inclusion bodies.

Further in another embodiment of the invention, the cytoplasmic TDP-43 inclusion bodies are ubiquitin positive.

Further in another embodiment of the invention, the mouse exhibits brain atrophy, neuronal loss and learning memory loss.

In another aspect, the invention relates to a cell or a tissue isolated or derived from the transgenic mouse as aforementioned.

Further in another aspect, the invention relates to a method for evaluating potential therapeutic effects of a compound for treating, preventing and/or inhibiting frontotemporal lobar degeneration with ubiquitin-positive inclusions (FTLD-U) in a mammal, comprising the steps of: a) administering the compound to a transgenic mouse whose genome comprises a transgene operably linked to a neuronal specific promoter effective for an increased expression of the transgene in the brain of the mouse, the transgene comprising a nucleotide sequence encoding TAR DNA-binding protein 43 (TDP-43); and b) determining the potential therapeutic effects of the compound on the transgenic mouse by identifying improvement in learning and memory behavior and/or motor function of the tansgeinc mouse.

Yet in another aspect, the invention relates to a method for identifying a candidate agent for treating, preventing and/or inhibiting FTLD-U, comprising the steps of: a) measuring the level of TDP-43 expression in the aforementioned transgenic mouse; b) administering the agent to the transgenic mouse; and c) measuring the level of TDP-43 expression in the transgenic mouse; wherein a decrease in the level of TDP-43 expression after treatment with the agent identifies the agent as a candidate agent for treating, preventing and/or inhibiting FTLD-U.

Further in another aspect, the invention relates to a neuronal cell comprising a transgene operably linked to a neuronal specific promoter effective for an increased expression of the transgene in the neuronal cell, the transgene comprising a nucleotide sequence encoding TAR DNA-binding protein 43 (TDP-43). The neuronal specific promoter may be selected from the group consisting of $Ca^{2+}$/calmodulin-dependent kinaseIIα (CaMKIIα) promoter, neuron-specific enolase (NSE) promoter and motor neuron-specific promoter.

In one embodiment of the invention, the neuronal cell exhibits TDP-43 protein inclusion bodies in the cytosol thereof.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Materials and methods
Construction and Generation of CaMKII-TDP-43 Transgenic Mice.

To generate the transgenic mice, an 1,245 bp, full length mouse TDP-43 cDNA (NCBI GenBank NM_145556; SEQ ID NO: 1) was cloned into the EcoRV site of pNN265, a modified form of pcDNAI/Amp kindly provided by Dr. Eric Kandel (Mayford et al., 1996). A 2.7 kb NotI fragment was isolated from pNN265 and cloned into the NotI site of the vector pMM403 containing 8.5 kb of the mouse CaMKII promoter region also provided by Dr. Eric Kandel (Mayford et al., 1996), resulting in pCaMKII-TDP-43. An 11.2 kb SfiI fragment was then purified from pCaMKII-TDP-43 and injected into the one-cell embryos of FVB/N mice. The offsprings were genotyped, and 10 out of 78 potential transgenic pups were identified to carry the transgene. These 10 founders were bred with FVB/N mice, and 3 of them were germ-line transmitted. Three homozygous TDP-43 Tg mouse lines were then generated by intercrosses of the three hemizygous lines individually. The homozygosity was determined by Southern blotting, and the overexpression of TDP-43 was confirmed by quantitative RT-PCR and Western blotting analyses of the forebrain tissues from 2-month-old mice. All the mice were bred at the Animal Facility of the Institute of Molecular Biology (IMB), Academia Sinica, Taiwan. They were housed in a room maintained on a 12 h/12 h light/dark cycle (light on at 7:00 a.m.) with a continuous supply of food and water. Experimental procedures for handling the mice followed the Guidelines of IMB, Academia Sinica.

For genotyping of the founders, both Southern blot analysis and PCR were performed according to standard procedures. For Southern blot analysis, the genomic tail DNAs were digested with KpnI and hybridized with a 543 by NotI fragment from pGEMT-TDP-43 (Promega). The genomic DNAs of the transgenic CaMKII-TDP-43 mice would give rise to a 4.4 kb fragment on the blot. For PCR, the following primers were used: forward primer 5'-GGC TTG AGA TCT GGC CAT ACA CT-3' (SEQ ID NO: 2) and reverse primer 5'-TAA GAT CTT TCT TGA CCT GAA CCA TA-3' (SEQ ID NO: 3). A 523 by band on gel was expected for the transgenic mice, but not the wild type or non-transgenic mice. The breeding test was used to confirm the homozygosity of the Tg(+/+) mice. Kuen-Jer Tsai and Che-Kun James Shen "Elevated expression of TDP-43 in the forebrain of mice is sufficient to cause neurological and pathological phenotypes mimicking FTLD-U" submitted October 2009 to *Journal of*

*Experimental Medicine* (status of which is in revision, which is herein incorporated by reference in its entirety).

In situ Hybridization.

In situ hybridization was performed as described previously (Tsai et al., 2002) with minor modifications. The coronal sections of the width 20 μm were taken from the mouse brains serially, covering both the hippocampus and cortex of the cerebrum. The antisense probe complementary to the sequence of the TDP-43 mRNA (5'-GCT CTG AAT GGT TTG GGA ATG AAG ACA TCT ACC ACT-3'; SEQ ID NO: 4) and the corresponding sense probe were 3' end-labeled with $\alpha[^{35}S]dATP$, and hybridized respectively at 42° C. for 24 hr with the brain sections on the Poly-Prep slides (Sigma). After extensive washing, the slides were dehydrated with ethanol and exposed to BioMax films (Kodak) for 10 days. The signals from the in situ hybridization were quantified by measuring the optic densities of the relevant fields with the use of the National Institutes of Health IMAGE program.

Morris Water Maze Task.

For spatial learning test, the Morris water maze task was carried out as described previously (Tsai et al., 2007). The animals were subjected to four trials per session and two sessions a day, with one session given in the morning and the other given in the afternoon. For a complete test, a total of 6 sessions in 3 days were given. The time spent by the individual mice to reach the platform in the water was recorded as the escape latency.

Novel Object Recognition Task.

The experimental protocol described by Cao et al. (2008) was used. Briefly, the mice were individually habituated to an open-field box for 3 days. During the training sessions, two novel objects were placed in the open field, and the animals were allowed to explore for 15 min. The time spent exploring each object was recorded. During the one-hour recall tests, the animals were placed back into the same box, in which one of the familiar objects during training was replaced by a novel object, and allowed to explore freely again for 15 min. The ratio of the time spent exploring any one of the two original objects (training session) or the novel one over the total time spent exploring both objects was used to measure the recognition function.

Fear Conditioning Task.

For fear conditioning task, mice were placed in a fear conditioning shock chamber (10×10×15 inches high) with multi-parameter activity monitors. The conditioned stimulus (CS) used was an 85 dB sound at 2,800 Hz, and the unconditioned stimulus (US) was a continuous scrambled foot shock at 0.75 mA.

Locomotor Activity.

Mouse movements were monitored by the TRuScan Digiscan system (Coulbourn Instruments, Inc.), which employed infrared beams to detect the horizontal and vertical movements. The pattern of the beam breaks was computerized to generate a quantitative measure of the locomotor activity. Each mouse was placed in the testing chamber for 5 min for adaptation, followed by a 30-min recording for analysis of the total time moved.

Limb-Clasping Observation and Rotarod Test.

The limb-clasping and rotarod tests were performed according to the procedures described by Hara et al. (2006). For the latter, mice were placed on a rod rotating at 20 r.p.m. and the time taken for them to fall from the rod was measured. If a mouse stayed on the rod until the end of the 2 min trial, a time of 120 sec was recorded.

Western Blotting.

Figure 4:
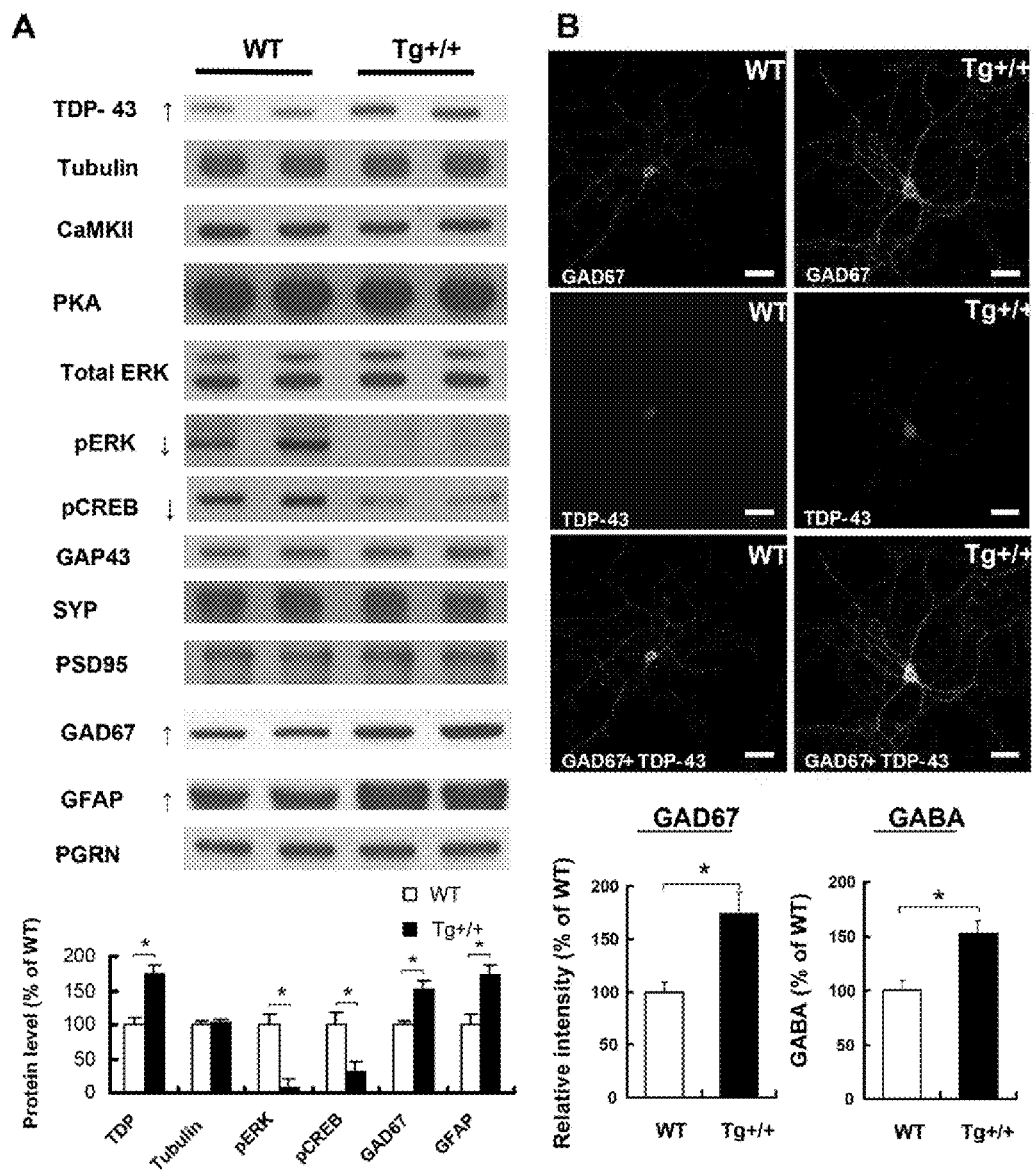
FIGS. 4A-4B show alterations of the levels of learning/memory associated proteins in CaMKII-TDP-43 Tg mice.

For analysis of the expression levels of different proteins (FIGS. 1C and 4A), the extracts were prepared from the cerebral cortex, hippocampus, cerebellum, and spinal cord of the wild type and male transgenic mice of two-month old by homogenization of the tissues in RIPA lysis buffer [Tris-HCl 50 mM, NaCl 150 mM, Igepal CA-630 1%, EDTA (pH8) 2 mM, $Na_3VO_4$ 1 mM, pepstain A 20 μg/ml, leupeptin 20 μg/ml, aprotinin 20 μg/ml, PMSF 1 mM, NaF 50 mM]. The extracts were then analyzed by 8-12% SDS-PAGE followed by blot hybridization with one or more of the following antibodies: a home-made anti-TDP-43 (Wang et al., 2008a), anti-tubulin (Upstate), anti-CamKII (Chemicon), anti-ERK (Upstate), anti-pERK (Upstate), anti-phosphorylated cAMP response element binding protein (pCREB) (Upstate), anti-GAD67 (Chemicon), anti-GAP43 (Chemicon), anti-GFAP (Chemicon), anti-PKA (Chemicon) and anti-PGRN (R&D Systems), respectively. The relative intensities of the bands were normalized against that of the tubulin and expressed as means ±SEM.

For the sequential biochemical fractionation analysis, the forebrain tissue was dissected, weighed, and sequentially extracted with buffers of increasing strength as previously described (Neumann et al., 2006). Briefly, the forebrains were extracted sequentially at 5 mL/g (volume/weight) with low salt (LS) buffer (10 mM Tris, pH 7.5, 5 mM EDTA, 1 mM DTT, 10% sucrose, and a cocktail of protease inhibitors), high salt-Triton (TX) buffer (LS+1% Triton X-100+0.5M NaCl), myelin floatation buffer (TX buffer containing 30% sucrose), and sarkosyl (SARK) buffer (LS+1% N-Lauroyl-sarcosine+ 0.5 M NaCl). The SARK insoluble materials were further extracted in 0.25 mL/g urea buffer (7M urea, 2M thiourea, 4% 3-[(3-Cholamidopropyl)dimethylammonio]-1-propanesulfonate (CHAPS), 30 mM Tris, pH 8.5). The proteins in the urea-soluble samples were resolved by Tris-glycine/12% SDS-PAGE, transferred to nitrocellulose, and then probed with anti-TDP antibody (Protein Tech Group) used before by others in similar experiments (Winton et al., 2008).

Immunostaining.

Immunostaining was used to examine the expression patterns of TDP-43 and GAD67 in primary hippocampal neuron cultures of the wild type and transgenic mice. Cells were dissected from E16.5 embryos for culturing in Neuralbasal medium, and the cultured cells (DIV 14) were fixed with 4% paraformaldehyde (PFA). For staining, cells were incubated overnight with individual primary antibodies against GAD67 (1:500) and TDP-43 (1:100), respectively, in 1% donkey serum (D9663, Sigma) in PBS (phosphate buffered saline).

For immunofluorescence staining of mouse brains, adult mice were anesthetized and perfused transcardially in PBS with 4% PFA. Brains were removed and immersed in 4% PFA solution with 20% sucrose overnight. Sections with a thickness of 12 μm were incubated with one or more of: anti-TDP-43 antibody (one was previously generated in our lab (Wang et al., 2008b) and another from the Protein Tech Group), mouse monoclonal anti-GFAP (Chemicon), mouse monoclonal anti-ubiquitin (Chemicon), mouse monoclonal anti-NeuN (Chemicon) and Alex488-conjugated goat anti-mouse antibodies (Molecular Probe). The sections were then incubated with DAPI and coverslipped with the mounting medium (Dako fluorescent mounting medium, Dakocytomation). All sections were examined in a laser scanning confocal microscope (LSM 510, Zeiss).

Electrophysiological Recordings.

Brain slices of wild type and TDP-43 Tg mice at 2 months of age were taken for the LTP experiments. Whole-cell voltage clamp recordings were performed on cultured hippocampal neurons (DIV 12-15) from wild type and TDP-43 Tg mice. Briefly, brains of wild type and TDP-43 Tg mice at 2 months of age were quickly removed and placed in cold cutting buffer. The hippocampus was sliced into 400 μm sections, submerged in artificial CSF (aCSF) buffer, and maintained for 1.5 h before recording. A bipolar tungsten-stimulating electrode was placed in the middle of the stratum radiatum layer of CA1 area, and the extracellular field potentials were recorded by a glass microelectrode (3 MΩ; filled with aCSF). The pulse duration was 100 μs and the test responses were elicited at 0.05 Hz (GS-3200; Gould, Cleveland, Ohio).

LTP was induced by two trains of 100 Hz stimulation each lasting for 1 s with a 20 s interval between them. The stimulation strength was set to provide field EPSPs (fEPSPs) with an amplitude that was 40-60% of the maximum. When the paired-pulse facilitation (PPF) was examined in the CA1 area, the stimulation was delivered at 0.01 Hz and the inter-stimulus intervals (ISIS) of 20, 50, 80, 100, 200, 300, 400, and 500 ms with the stainless-steel bipolar electrodes placed in the outer and inner molecular layers, respectively, of the piriform cortex. fEPSPs from the corresponding layers were recorded via the glass pipettes, and they were amplified and filtered at 1 kHz. The PPF ratio was calculated by dividing the amplitude of the second fEPSP by that of the first fEPSP.

Whole-cell voltage clamp recordings were performed on the hippocampal neurons cultured for 12- to 15 days using an Axopatch 200B amplifier (Molecular Devices, Union City, Calif.). For the miniature post-synaptic current (mEPSC) experiments, 1 μM tetrodotoxin was added to the bath to suppress the action potentials. Only those cells which had a resting membrane potential of <−50 mV, stable capacitance, and resistance throughout the experiment were considered. The data recorded were digitized with Digidata 1322A (Molecular Devices) and analyzed with Clampfit 9.2 (Molecular Devices).

GABA Analysis.

To measure the brain GABA levels, the mouse brains were quickly dissected on a chilled dissection board, homogenized on ice (50 mg of tissue with 1 ml of 400 mM $HClO_4$ and 50 μM EDTA), and neutralized with 100 mM borate buffer (1:10). The homogenates were then centrifuged (14,000 rpm, 15 min, 4° C.) and filtered with Ultrafree-MC centrifugal filter units (Millipore, 14000 rpm, 1 min, 4° C.). The concentrations of GABA were then determined by HPLC.

Magnetic Resonance Imaging (MRI) Measurement.

MR1 was acquired in a 7.0 Tesla MRI system (Bruker Companies, Ettlingen, Germany). High resolution T2-weighted images (T2WIs) were acquired for the whole brain region of each mouse using a 3D-RARE (Rapid Acquisition with Relaxation Enhancement) sequence with a field of view of 200×150×100 $mm^3$ and a matrix size of 200×150×65 $mm^3$, yielding a voxel size of 100×100×154 $μm^3$. The repetition time (TR) and the echo time (TE) were 2,500 ms and 32 ms, respectively. The region of the hippocampus was selected manually from slice to slice, and the volume was then calculated by a homemade code using the MATLAB.

Neuronal Counts.

To quantitate and compare the numbers of the cortical neurons among the WT and Tg mice, comparable coronal brain sections derived from the septo-striatal, septo-diencephalic, or the caudal diencephalon regions of the cerebral cortexes were immunostained with antibody (anti-NeuN) against the neuronal marker NeuN. The numbers of the neurons in a total of six comparable areas (2-3 adjacent fields for each area) were counted. The neuronal counts for Tg mice were then normalized to WT mice (100%).

TUNEL Assay.

For TUNEL assay, trypsinized brain sections were reattached on 0.01% polylysine-coated slides, fixed with 4% formaldehyde solution and fluorescence stained following the protocols of the DeadEnd fluorometric TUNEL system (Promega). The stained samples were analyzed under a fluorescence microscope, and the signals counted in randomly selected views.

Survival analysis.

The wild type and the TDP-43 Tg(+/+) mice born between March 2006 and December 2008 were used to compare the lifespan/survival rates. Five per cage of the animals were maintained in a pathogen-free environment at the Animal Facility of the Institute of Molecular Biology (1 MB), Academia Sinica, Taiwan. The dates of birth and death of each mouse were recorded. The survival curves were drawn by the Kaplan and Meier method, and compared by the Log-rank test.

Statistical Analysis.

All data are reported as the mean±S.E.M. Independent experiments were compared by the Student's t-test. Differences, indicated by the asterisks, were considered statistically significant at $p<0.05$.

Results

Generation of Tg Mice

To test whether elevated expression of TDP-43 in the forebrain could be a cause for the generation of the various disease phenotypes as observed in FTLD-U patients, we have constructed transgenic mouse lines carrying full-length mouse TDP-43 cDNA under the transcription control of a 8.5 kb promoter region of the $Ca^{2+}$/calmodulin-dependent kinase II, CaMKII, gene (Mayford et al., 1996) (FIG. 1A). Genotyping by PCR and Southern blotting were used to identify the transgene-positive mice of the founders and their progenies, as exemplified in FIG. 1B. DNA samples from both the heterozygotes(+/−) and homozygotes(+/+) of the transgenic (Tg) mice gave a 523 by band in the PCR analysis and a 4.4 kb fragment in the Southern blotting analysis. Neither band was present in the non-transgenic (NT) samples (FIG. 1B). The identities of the homozygotes of the Tg mice were also confirmed by breeding them with the NT mice (data not shown).

Three independent transgenic (Tg) lines were generated and they exhibited similarly elevated levels of TDP-43 expression (approximately 2-fold higher than the non-transgenic mice), as directed by the CaMKII promoter, in the cortex and hippocampus, as detected by the Western blotting analysis (top 2 panels, FIG. 1C). On the other hand, the TDP-43 protein levels in the cerebellum and spinal cord of the Tg mice were similar to those of the wild type (WT) mice (bottom 2 panels, FIG. 1C). As confirmed by in situ hybridization experiments, the wild type mice exhibited basal signals whereas the TDP-43 Tg mice showed higher signals in both the hippocampus and cortex (FIG. 1D). As expected, both the endogenous (left panel, FIG. 1E) and the overexpressed, exogenous TDP-43 proteins (right panel, FIG. 1E) were present in the hippocampus mainly in the neuronal layers, as shown by immunohistochemical staining.

FIG. 1A shows a physical map of the CaMKII-TDP-43 fragment for pronuclei injection. The orientation of transcription is indicated by the arrow. The positions of the short hybrid intron derived from an adenovirus splice donor, an immunoglobulin G splice acceptor, and the SV40 poly(A) addition sequence (pA) are indicated. The approximate locations of the Southern blotting- and PCR probes, are also indicated. Transgenic mice were identified by the presence of the 4.4 kb KpnI fragment on the Southern blot and the 523 by PCR band on gel. The restriction sites on the map are: K, KpnI; E, EcoRV; N, NotI; S, SfiI. The 3'-untranslated region of CaMKIIa is a cis-acting signal for the localization and translation of mRNA in dendrites." Two regulatory introns are disclosed in Choi et al., (1991) "A generic intron increases gene expression in transgenic mice" *Mol Cell Bio*/11:3070-3074.

FIG. 1B shows genotyping of the transgenic mice. The data from PCR (top panel) and Southern blotting (bottom panel) analysis of the tail DNAs are exemplified. (+/+) and (+/−) represent the homozygotes and heterozygotes of the transgenic mice (Tg), respectively. NT represents the non-transgenic samples.

FIG. 1C shows Western blotting of the protein extracts from the hippocampus, cortex, cerebellum, and spinal cord of the wild type (WT), non-transgenic (NT), and transgenic (Tg) mice, respectively. Note the higher levels of TDP-43 in the hippocampus and cortex samples from the Tg mice. The similar levels of the TDP-43 protein in the hippocampus or cortexes of the Tg(+/−) and Tg(+/+) mice might be due to a feedback regulatory mechanism on the protein level, since the TDP-43 mRNA level of the Tg(+/+) mice was approximately 2-fold of that of the Tg(+/−) mice (FIG. 8). The details of this observation await to be examined.

FIG. 1D shows in situ hybridization patterns of TDP-43 transcripts in the brains of wild type (WT) and TDP-43 Tg mice (Tg). Note the higher expression levels in the hippocampus and cortex of the Tg mice. (E) Immunostaining patterns of TDP-43 protein in the brains of WT and Tg mice. CA1, CA 1 layer; CA3, CA3 layer; DG, dentate gyrus. Results in B to E are representative of three independent experiments.

Figure 8A:
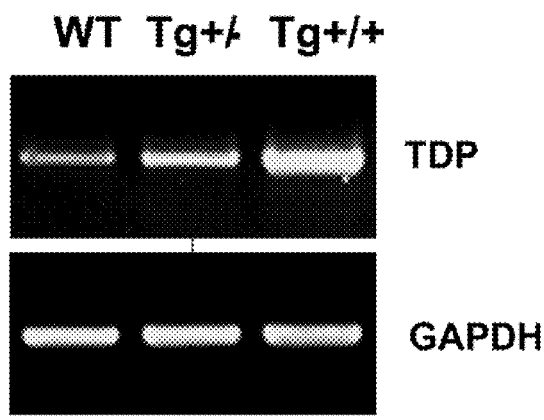
FIGS. 8A-8B show the levels of TDP-43 in the TDP-43 Tg(+/+) and Tg(+/−) mice in comparison to the wild type (WT).
Figure 8B:
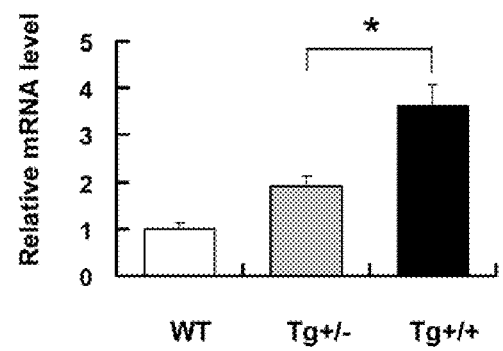

FIG. 8A shows representative gel pattern of RT-PCR analysis of the brain RNAs, FIG. 8B is a histograph showing the levels of the brain TDP-43 mRNAs of Tg(+/+) and Tg(+/−) mice relative to the WT mice. The results are the mean±SEM of three independent experiments, and N is 5 for each of the three groups.

Figure 2:
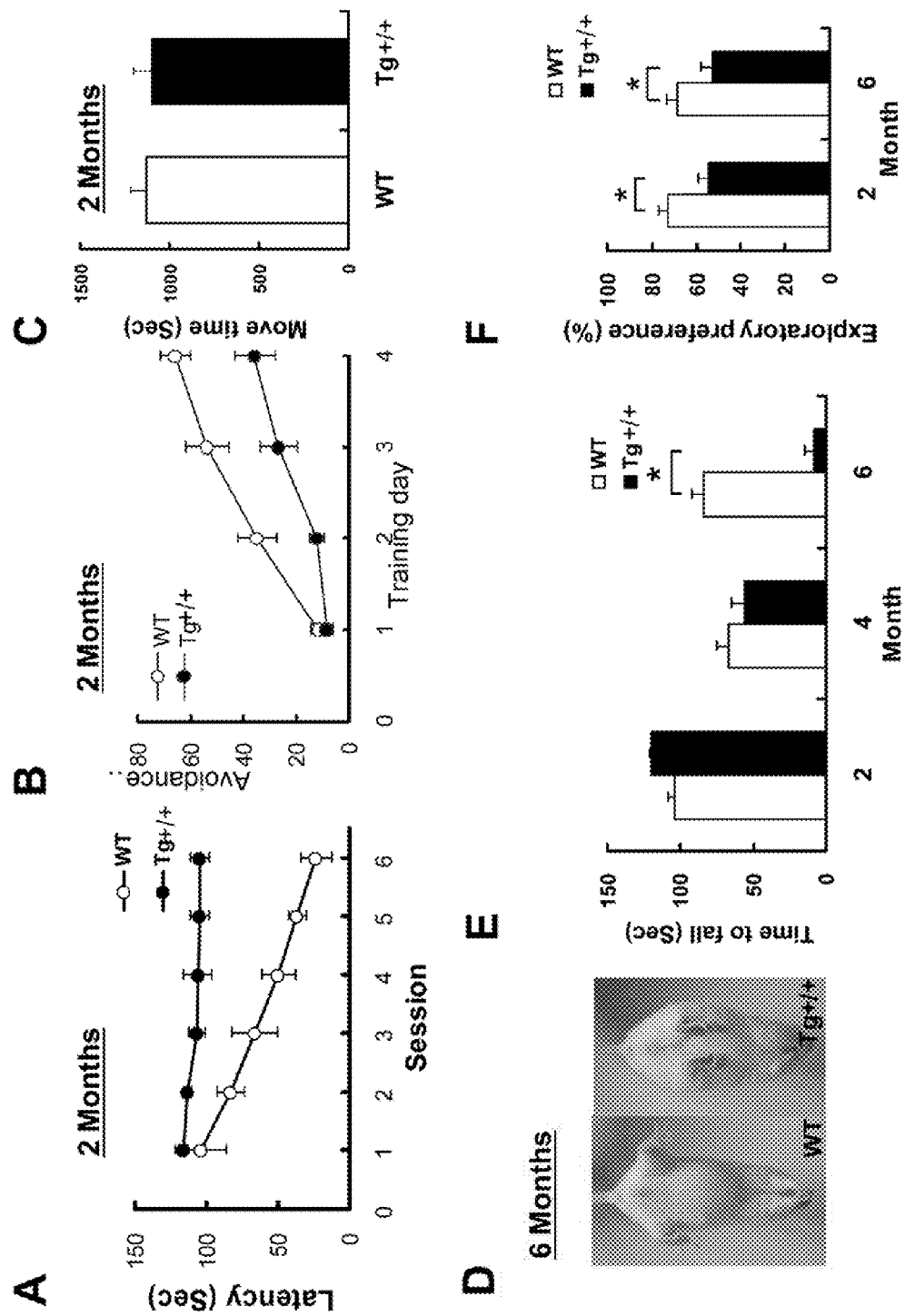
FIGS. 2A-2F show behavioral performances of CaMKII-TDP-43 Tg mice.
Figure 9:
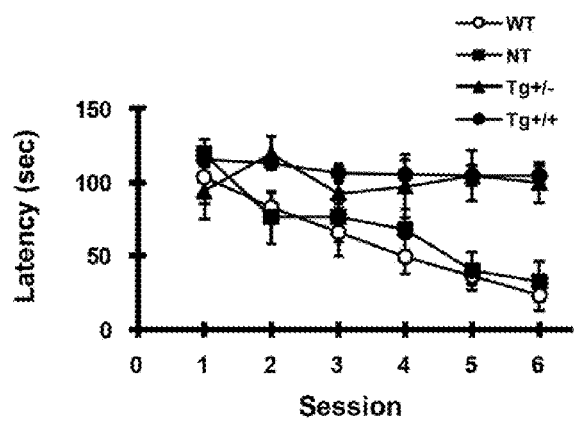
FIG. 9 shows the results of water maze tests of CaMKII-TDP-43 Tg(+/−) mice in comparison to the wild type (WT), non-transgenic (NT), and TDP-43 Tg(+/+) mice.

Impaired Performances of the TDP-43 Tg Mice in Morris Water Maze and Fear Conditioning Tasks The water maze task was used to evaluate whether overexpression of TDP-43 in the hippocampus and cortex affected the learning/memory of the mice. As shown, the 2-month old Tg(+/+) mice exhibited significantly impaired performance in the test (compare the latencies of the Tg mice to those of the wild type mice in FIG. 2A, and to the non-transgenic littermates as shown in FIG. 9. Since the heterozygous (+/−) and homozygous (+/+) Tg mice exhibited similar extents of impairment in their learning/memory capabilites (FIG. 9), the homozygous Tg(+/+) mice were used for all subsequent behavior tests and other experimental analyses. As shown in FIG. 2B, the impairment of the learning/memory capabilities of the Tg(+/+) mice were also revealed by the fear-conditioning task. Thus, the data from these two cognition tests together indicated that overexpression of TDP-43 in the hippocampus and cortex of the mice significantly impaired their learning/memory capabilities.

FIG. 9 shows the results of water maze tests of mice of the age 2 months were carried out. The learning/memory capabilities are expressed as the latencies exhibited in six consecutive sessions. There was no significant difference of the littermates between Tg(+/−) and Tg(+/+) mice. Results represent the mean±SEM of three independent experiments and N is 20 for each of the four groups.

Abnormal Limb-Clasping and Impaired Performance of TDP-43 Tg Mice in Rotarod Tests The motor functions of the TDP-43 Tg mice were also analyzed. The Tg mice were born normally and their spontaneous locomotor activities were normal at the age of two months (FIG. 2C). However, at the age of six months, TDP-43 Tg mice showed limb-clasping reflexes when being suspended by tails, whereas the control mice extended their limbs (FIG. 2D). This abnormal reflex was often observed in mouse models of other neurodegenerative diseases, e.g., the Huntington disease (HD). The mice were further subjected to the rotarod test, and the result indicated that they were severely impaired in the motor coordination, balance and grip strength at the age of 6 months (n=10; p<0.05), but not at the age of 2 months or 4 months (FIG. 2E). The data of FIG. 2C-E showed that the TDP-43 Tg mice developed progressive motor behavioral deficits at the age of six months. Because of the deficiency of the motor functions of the 6-month old TDP-43 Tg mice, the mice were also subjected to the novel object recognition test. As shown in FIG. 2F, the 6-month old TDP-43 Tg mice were still deficient in the learning/memory capabilities, just like the 2-month old Tg mice.

FIG. 2A shows water maze tests of the wild type (WT) and TDP-43 Tg mice of the age 2 months. The learning/memory capabilities are expressed as the latencies exhibited in six consecutive sessions of the test. Results represent the mean±SEM of three independent experiments and N is 20 for each group. FIG. 2B shows the results of comparison of the cognitive functions of 2-month old, WT and Tg mice in the fear conditioning task. FIG. 2C shows locomotor activity test of 2-month old WT and Tg mice. Results in FIGS. 2B and 2C represent the mean±SEM of three independent experiments and N is 16 for each group. FIG. 2D shows abnormal limb-clasping of a 6-month old Tg mouse in comparison to a WT mouse when suspended by their tails. Results are representative of five independent experiments. FIG. 2E shows the results of rotarod tests of WT and Tg mice. The time until drop from the rotating rod (20 r.p.m.) are shown for three different ages of mice. Note the progressive loss of the motor function of the Tg mice at the age of 6 months. FIG. 2F shows performance of mice in one-hour novel object recognition tests. Note the reductions of the learning/memory capabilities of both the 2-month (18%) and 6-month (16%) old Tg mice when compared to the WT mice. The results represent the mean±SEM of three independent experiments and N is 10 for each group. *p<0.05.

Electrophysiology Analysis of TDP-43 Tg Mice

In view of the impairment of the learning/memory of the TDP-43 Tg mice, we have carried out electrophysiology analysis of their Long-term potentiation (LTP) in comparison to the wild type mice. LTP between the Schaffer collaterals and principal CA1 pyramidal neurons in the hippocampal slices prepared from the mice were measured. In correlation with the learning/memory test experiments (FIG. 2), tetanic stimulation of the Schaffer collaterals resulted in robust LIP in slices from the wild type mice. However, the slices from the TDP-43 Tg mice had impaired LTP maintenance for 60 min after the LTP induction (FIG. 3A).

Miniature excitatory post-synaptic current (mEPSC) was recorded from DIV 12-15 cultured hippocampal neurons (FIG. 3B). No significant difference in the mEPSC frequencies could be detected (WT 3.16±0.65; Tg 4.59±0.83, p=0.20, FIG. 3B). However, significant difference existed between the mEPSC amplitudes of the wild type and Tg mice (WT 47.30±2.56; Tg 39.52±2.96, *p=0.03, FIG. 3B). Significant difference in the decay time constant (WT 3.18±0.30; Tg 4.99±0.25, ***p=0.0006, FIG. 3B) was also detected but not the rise time constant (WT 1.80±0.08; Tg 1.81±0.04, p=0.88, FIG. 3B). These data indicated that the receptor gating properties contributing to the EPSC amplitude and decay kinetics were altered in the TDP-43 Tg mice.

FIG. 3A shows attenuated LTP in the hippocampus of 2-month old CaMKII-TDP-43 Tg mice. LTP was induced by strong tetanus stimulation in the stratum radiatum layer of CA1. Note inhibition of the induction and maintenance of LTP in the TDP-43 Tg mice. Results represent the mean±SEM of three independent experiments and N is 8 for each group. FIG. 3B shows altered mEPSCs recording in the primary hippocampal culture of CaMKII-TDP-43 Tg mice. Whole-cell voltage clamp recordings of cultured hippocampal neurons (12-15 DIV) from the wild type and TDP-43 Tg mice were carried out. Representative traces of the mEPSCs recorded from the neurons are shown on top. Note the less number of the major peaks (arrows) in the Tg(+/+) sample than the WT sample. The frequencies, amplitudes, decay Tau, and rise Tau of the mEPSCs are shown in the 4 histograms, respectively. $*p<0.05$; $***p<0.001$. The 2 scale bars are 50 pA and 1 s, respectively. Results represent the mean±SEM of three independent experiments and N is 10 for each group.

Decreased Levels of pERK and pCREB, and Increased Levels of GFAP, GAD67 and GABA in the Hippocampus and Cortex of TDP-43 Tg Mice In view of the impaired performances of the TDP-43 Tg mice in the learning/memory tests and their lowered LTP (FIGS. 2 and 3), we have checked the levels of several major candidate proteins in the hippocampus and cortex known to be involved in different signal transduction pathways regulating the learning/memory. While the protein amounts of CaMKII, protein kinase A (PICA), growth-associated protein 43 (GAP43), synaptophysin (SYP) and postsynaptic density 95 (PSD95) were similar between TDP-43 Tg mice and the wild type controls, the levels of both pERK and its downstream target pCREB in the TDP-43 Tg mice were decreased, as shown by Western blots and histogram in FIG. 4A.

It should be noted that the level of progranulin (PGRN) in the forebrains of the Tg mice was similar to that of the WT mice (FIG. 4A). It is not clear at the moment why the level of PGRN was not increased in the FTLD-U mouse brains in view of the elevated level of brain GFAP/gliosis in these mice. PGRN is expressed in neurons and microglia within the central nervous system, and it is elevated in microglia during glyosis. Interestingly, in recent models of nerve injury, it was found that axotomy caused both increase of TDP-43 and decrease of PGRN in the neurons whereas the level of PGRN in the surrounding activated microglia was increased. Thus, likely there could also be an decrease of PGRN in the TDP-43 overexpressing neurons of the Tg mouse forebrains, which would compensate for the increase of the PGRN amount in the activated microglia. Future experimentation should clarify this point.

Interestingly, the protein levels of the glutamic acid decarboxylase 67 (GAD67) and glial fibrillary acidic protein (GFAP) were also increased, by approximately 2-fold, in the cortex and hippocampus of the TDP-43 Tg mice. Of the two, GAD67 was known as the principal enzyme for synthesis of the major inhibitory neurotransmitter γ-aminobutyric acid (GABA) in the brain. Its elevated expression in TDP-43 Tg mice was further confirmed by double immunostaining of GAD67 and TDP-43 in the primary neuron cultures from both the Tg mice and the controls (FIG. 4B). Higher immunostaining signals of GAD67 were present in both the soma and the processes of the neuronal cells of the Tg mice than those of the wild type controls (compare the right 3 panels to the left 3 panels, FIG. 4B), while the levels of the neuron-specific nuclear protein (NeuN) were similar between the Tg and control mice (data not shown). In consistency with the immunostaining data of GAD67, release of the GABA neurotransmitter was also increased in the forebrains of the TDP-43 Tg mice (lower right panel of FIG. 4B). The results of FIGS. 4A-4B suggested that overexpression of TDP-43 impaired the learning/memory of the TDP-43 Tg mice in part by disruption of the phosphorylation of ERK as well as by upregulation of the inhibitory neurotransmitter GABA.

FIG. 4A shows representative patterns of the Western blot analysis comparing the levels of different proteins in extracts prepared from isolated cerebral cortex and hippocampus of 2 each of the WT and Tg mice of the age 2 months. Note the lower levels of pERK and pCREB, and higher levels of GAD67 and GFAP in the brains of the Tg mice. Results are representative of three independent experiments. FIG. 4B shows immunostaining analysis of GAD67 expression and measurement of GABA release. The primary hippocampal neuron cultures of the wild type (WT, left panel) and TDP-43 Tg (Tg, right panel) mice were double-stained with anti-GAD67 (green) and anti-TDP-43 (red). The scale bars are 50 μm long. Note the higher image signals of both GAD67 and TDP-43 in the Tg neurons. The statistical comparison of the relative GAD67 intensities of GAD67-positive cells of the WT and Tg mice is shown in the left histogram below the confocal image panels. The data represent the mean±SEM of three independent experiments and N is 20 for each group. Shown in the lower right histogram is the statistical comparison of the GABA levels of the WT and Tg mice. On the average, the GABA level in the Tg mouse forebrains was 50% higher than the WT mice (N=5, $p<0.05$).

Neuropathology of the TDP-43 Tg Mouse Brains

In addition to the behavioral, electrophysiological, and gene expression abnormalities described above in FIGS. 2-4, the TDP-43 Tg mice also exhibited several neuropathological characteristics similar to those of the FTLD-U patient brains. Firstly, reactive gliosis manifested by increased expression of the astrocytic marker GFAP has been known as a prominent pathological feature of FTLD. As shown by Western blotting, the level of the GFAP protein was increased in the TDP-43 Tg mice (bottom panel of FIG. 4A). Consistent with this, pronounced increases of the signals of anti-GFAP immunostaining were observed in both the hippocampus (HP) and the cortex (CX) of the Tg(+/+) mice as compared to the WT controls (FIG. 5A).

Secondly, Western blotting analysis revealed the presence of high molecular weight TDP-43 species, presumably the poly-ubiquitinated TDP-43, as well as the enrichment of the kDa and 35 kDa fragments in the urea-soluble fraction of brain extracts from the 6-month old Tg mice (FIG. 5B). This pattern on the Western blot was much less prominent in samples prepared from the 2-month old Tg mice and was not observed in those prepared from the WT mice (FIG. 5B).

FIG. 5A shows representative immunofluorescent images showing the increased GFAP staining (green) in the hippocampus and cortex (CX) of a TDP-43 Tg mouse as compared to an age-matched (2-month old) wild type control. Nuclei were labeled by DAPI (blue). CA 1, CA1 layer; CA3, CA3 layer; DG, dentate gyrus. The scale bars are 100 μm long. FIG. 5B shows representative Western blotting patterns of the urea-soluble fractions of the brain extracts from the cortexes and hippocampi of the wild type mice (WT) and Tg(+/+) mice of the age 2 months and 6 months, respectively. Note that the high molecular weight TDP-43 species (***) and the 25 kDa (*) as well as the 35 kDa (**) fragments of TDP-43 are prominent in the 6-month old Tg(+/+) mice, but not in the 2-month old mice. The 65 kDa band (open triangle) has also been observed by others on immunoblots of extracts from cell lines and from patient lymphocyte lysates, but its significance is unclear yet. The arrow points to the un-modified form of TDP-43. The term "Long Exp." Stands for long exposure; "Short Exp." Stands for short exposure of the blots. Results in FIGS. 5A-5B are representative of five independent experiments.

Immunofluorescence staining was also carried out to examine the sub-cellular distribution of TDP-43 in the Tg(+/+) mouse brains in comparison to the WT mice. As shown in FIG. 6A, TDP-43 was mainly detected in the nuclei, which were positively stained with both anti-NeuN and DAPI, of unaffected neurons of the TDP-43 Tg mouse brains. Notably, however, TDP-43 was absent from the nuclei of neurons with TDP-43(+) NCIs (arrows in the lower left 2 panels of FIG. 6A). The TDP-43(+) NCIs were not observed in the brains of the WT mice, as exemplified in the right four panels of FIG. 6A. Overall, approximately 15-20% of the neurons in the cortexes of the Tg(+/+) mice contained TDP-43(+) NCIs. Finally, anti-ubiquitin immunostaining showed that TDP-43(+) NCIs in the 6-month old Tg mouse brains were also positive for the presence of ubiquitin (FIG. 6B). Overall, the patterns from the proteinopathy analysis of the TDP-43 Tg mice, as displayed in FIGS. 5B and 6, were strikingly similar to those reported for the pathological FTLD-U brain samples with TDP(+)-UBIs.

FIG. 6A shows the brain sections of the WT and Tg mice were co-stained with anti-TDP-43 (red), anti-NeuN (green) and DAPI (blue). Note the presence of TDP-43(+) NCIs in the Tg mouse brains, as indicated by the arrows in the lower left two panels, but not in the WT mouse brains (right 4 panels). One neuron each in the Tg(+/+) and WT samples (boxed) was magnified in the lower right corners for better visualization. FIG. 6B shows representative immunostaining pattern of a 6-month Tg(+/+) mouse brain section exhibiting neuronal cells with TDP-43 (green)-containing NCIs that are also positive for the anti-ubiquitin (Ub) staining (red) (the arrows). High magnification photos of one of the cells with TDP-43 (+), Ub(+) NCIs are shown in the lower right corners of the 3 panels.

Brain Atrophy of the Tg Mice

Figure 7:
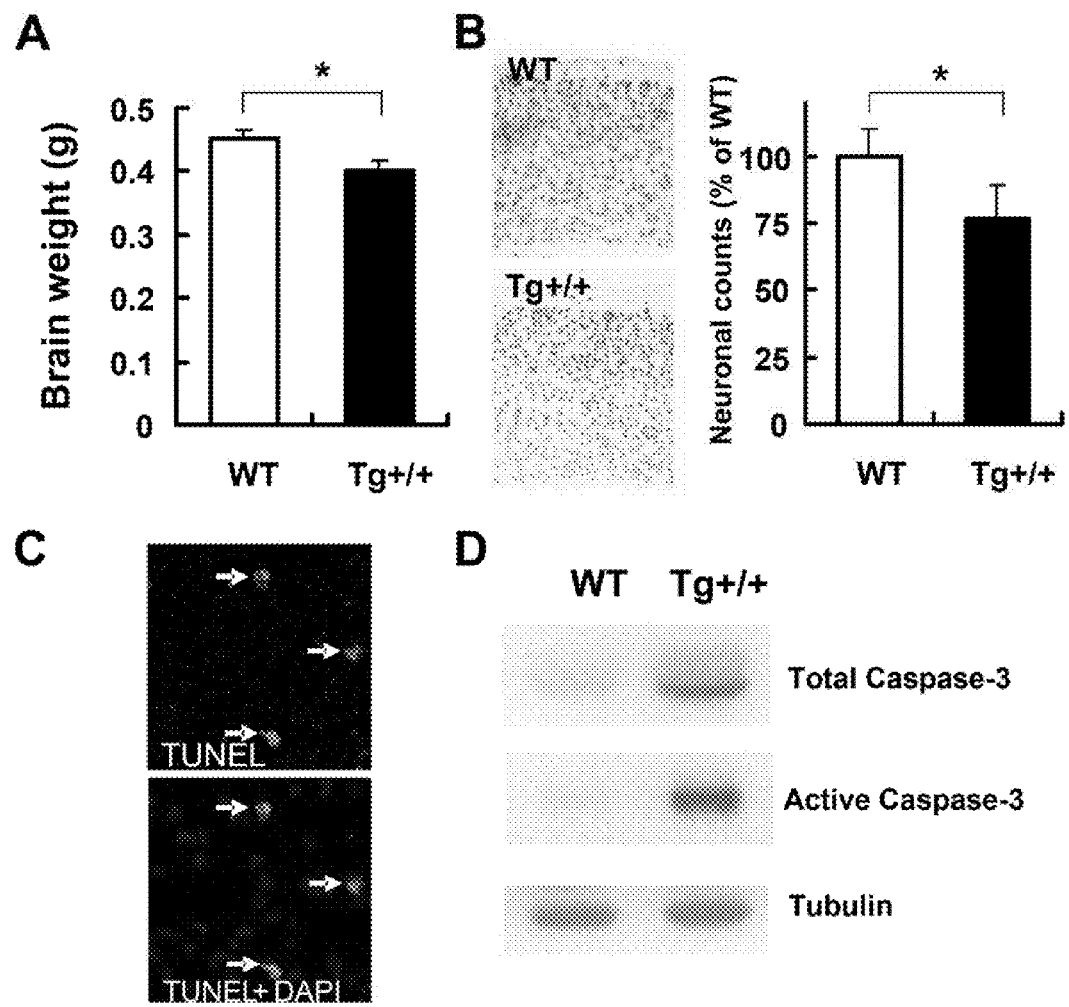
FIGS. 7A-7D show neuronal loss and apoptosis in the brains of the Tg mice.

To examine whether brain atrophy developed in the Tg mice as in the FTLD-U patients, MRI was used to measure the volume of the mouse hippocampus. The result showed that the volumes of the hippocampi of 6-month old Tg mice were 17% less than those of the control mice (N=5 for each group, p<0.05). This range of the shrinking was in interesting similarity to that of the frontal and temporal atrophy observed in some of the FTLD patients. In parallel with the MRI study, the brain weights and the cortex neuronal numbers of the mice were also examined. The results showed that there was a neuronal loss in the 6-month Tg mice. On the average, the brain weight of the Tg mice was 12% (N=5, p<0.05) less than that, of the WT mice (FIG. 7A) and the number of the cortical neurons was reduced by 24% (FIG. 7B). The neuronal loss might result in part from apoptosis of the neurons in the Tg mouse brains. Indeed, apoptotic nuclei were detected by TUNEL staining in the brains of the 6-month Tg(+/+) mice (FIG. 7C) and this was accompanied with increases in the amounts of both the total caspase-3 and active caspase-3 (FIG. 7D).

FIG. 7A shows reduction of the brain mass of the 6-month Tg mice. The whole brains from the mice were dissected and weighed. N=5, p<0.05. FIG. 7B shows loss of neurons in the cortexes of the Tg mice. Coronal brain sections from 6-month old Tg and WT mice were immunostained with anti-NeuN, as exemplified in the left 2 panels. The average number of the neurons in the cortexes of the Tg mice was compared with that of the WT mice (right panel; N=5 for each group and p<0.05). FIG. 7C shows TUNEL assay of the brains of 6-month old Tg mice. The green signals represent the apoptotic nuclei (the arrows), and the blue ones are from DAPI staining. Note that the apoptotic nuclei were not detected in the cortexes of either WT mice or 2-month old Tg mice (data not shown). FIG. 7D shows increases in the amounts of total caspase-3 and active caspase-3 in the brains of the 6-month old Tg mice. The total extracts from the (cortexes+hippocampi) of the mouse brains were analyzed by Western blotting.

Life Span of the Tg Mice

Figure 10:
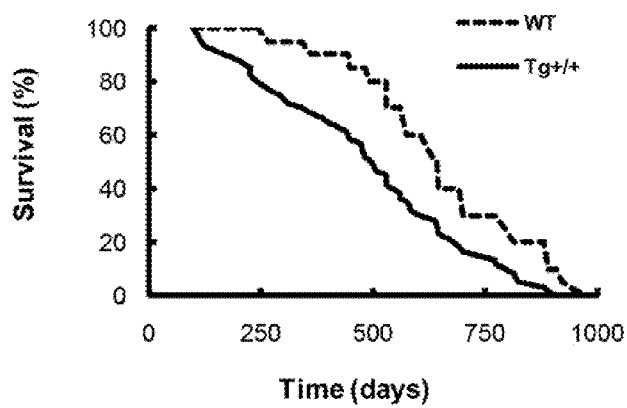
FIG. 10 shows the survival curves of the TDP-43 Tg(+/+) and wild type (WT) mice.

The survival rates of the mice were measured. The data, as shown in FIG. 10, indicated that the Tg(+/+) mice had shorter lifespan, with an average survival of 495 days, than that of the wild type ones, which had an average survival of 632 days. In FIG. 10, the survivals of the mice were followed up as described in the Supplementary Materials. The data were treated by the log-rank analysis ($X^2=9.8$, $p<0.01$). Note the significant drop of the average survival of the Tg(+/+) mice (495 days) when compared to the WT mice (632 days). N is 60 for each of the two groups.

Discussion

The invention relates to transgenic (Tg) mice with overexpression of mouse TDP-43 in the central nervous systems, including the hippocampus and cortex, under the control of the CaMKII promoter. This promoter has been used before to overexpress other proteins in mice and thus establish different mouse models. However, each of these transgenic mouse models exhibits unique phenotypes. For example, overexpression of either CREB or NR2b enhances the learning/memory capabilities of the mice, in consistency with the known roles of these factors in learning/memory. On the other hand, overexpression of the methyl-CpG binding protein 2 (MeCP2) leads to a motor dysfunction phenotype but it has no effect on the cognitive function of the mice. Noteworthily, CaMKII promoter-directed overexpression does not necessarily affect the mouse behaviors, as exemplified by the transgenic mice study of the sulfonylurea receptor, or SUR. In the case of TDP-43, its overexpression has resulted in a number of molecular, cellular, and phenotypic changes of the mice. These changes include impairment of learning/memory capabilities, progressive loss of the motor neuron function, abnormal LTP from electrophysiological measurements, an increase in gliosis, alternation of the expression levels of proteins known to be involved in learning/memory, reduction in hippocampus volume, and notably TDP-43(+)-UBI associated proteinopathological features (Table 1). These changes in the CaMKII-TDP-43 Tg mice are strikingly similar to the neurological and pathological features of the FTLD-U patients. Table is a summary of the molecular, cellular, and behavioral changes in TDP-43 Tg(+/+) mice as compared to the wild type.

Figure 11:
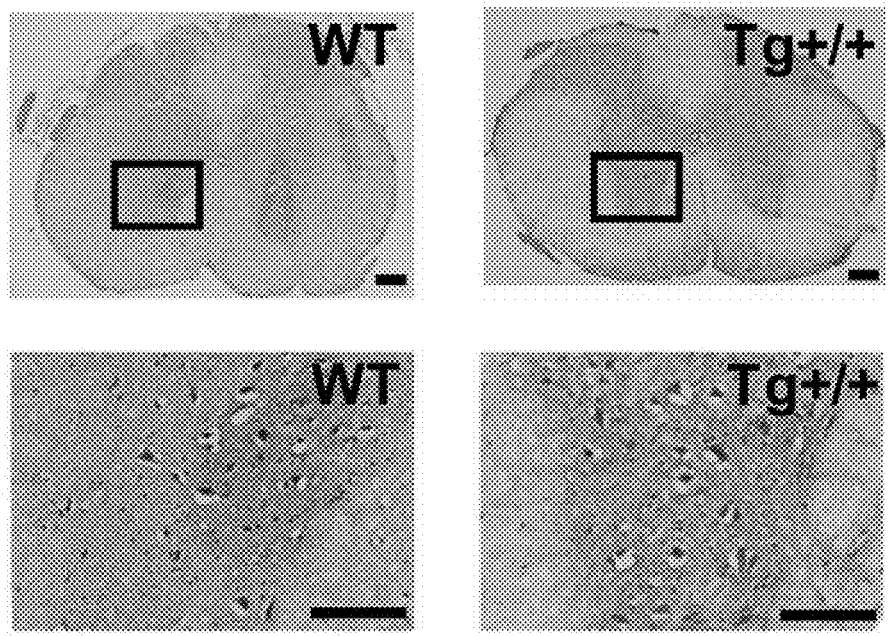
FIG. 11A-11B show histological analysis of the motor neurons in TDP-43 Tg(+/+) mice.
Figure 11:
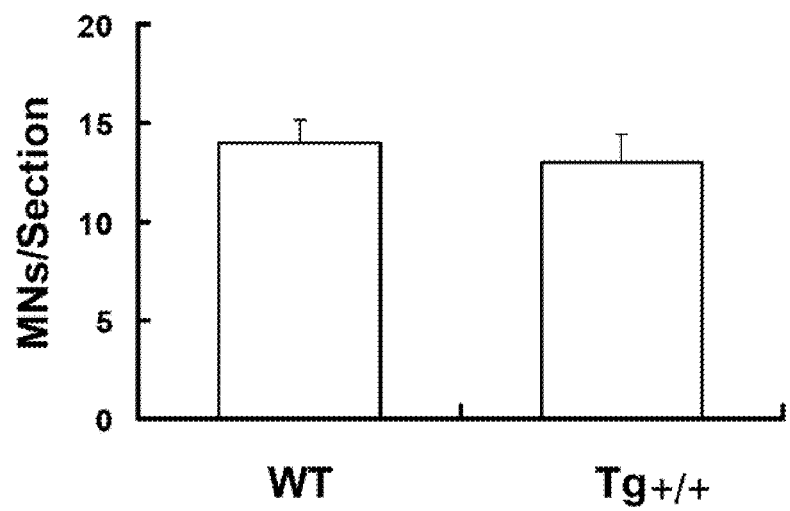

The Tg mice have displayed a pattern of age-dependent loss of motor function. With respect to this, the FTLD and the motor neuron disease, or MND, appear to overlap at several levels, and the FTLD patients share clinical features of MND. It should be noted here that only a portion of the FTLD patients would develop MND. Development of motor behavioral deficits in the TDP-43 Tg mice at the age of six months (FIGS. 2D and 2E) parallels the progressive loss of the motor function in the FTLD patients. As deduced from studies of different MNDs including amyotrophic lateral sclerosis (ALS), MND could be clinically manifested by signs and symptoms due to degeneration of the upper motor neurons in the motor cortex, lower motor neurons in the brainstem and spinal cord, or both. However, the sizes and numbers of the motor neurons in the spinal cords of the Tg mice are not significantly different from those of the wild type (FIG. 11). This is not surprising in view of the forebrain neuron-specificity of the CaMKII promoter used by us. Thus, the motor dysfunction of the CaMKII-TDP-43 Tg mice most likely have resulted from damage in the neuronal circuit in the forebrain, which includes the not so well-defined rodent motor cortex, and the corticospinal tract, caused by the CaMKII promoter-directed TDP-43 overexpression. It could also be possible, but relatively unlikely due to the CaMKII promoter specificity, that the motor dysfunction originated from some defects in the muscle of the Tg mice. Future detailed analysis of the CaMKII-TDP-43 Tg mice could clarify and differentiate among the above possibilities.

TABLE 1

|  |  | 2-month Tg | 6-month Tg |
|---|---|---|---|
| Cognitive functions | Water maze test | ↓ | na |
|  | Fear conditioning task | ↓ | na |
|  | Novel object recognition test | ↓ | ↓ |
| Motor functions | Limb-clasping reflex | ~ | ↑ |
|  | Rotarod testing | ~ | ↓ |
| LTP |  | ↓ | na |
| Gliosis | Anti-GFAP staining | na | ↑ |
| Expression levels of specific proteins | pERK | ↓ | ↓ |
|  | pCREB | ↓ | ↓ |
|  | GAD67 | ↑ | ↑ |
|  | GFAP | ↑ | ↑ |
| Presence on Western blot of urea-soluble fraction of the brain extracts | Poly-ubiquitinated TDP-43 | ↑ | ↑↑↑ |
|  | Phosphorylated TDP-43 | − | − |
|  | 35 kDa fragment of TDP-43 | ↑ | ↑↑↑ |
|  | 25 kDa fragment of TDP-43 | − | + |
| TDP-43(+) NCIs adjacent to TDP-43 depleted nuclei in Tg mouse brain sections | Immunohistochemistry | − | + |
| Presence of TDP-43(+), ubiquitin(+) NCIs | Immunostaining | − | + |
| Hippocampus volume | MRI measurement | na | ↓ |
| Neuronal loss | Brain weight | ~ | ↓ |
|  | Neuronal counts | ~ | ↓ |
| Apoptosis | TUNEL assay | − | ↑ |

↑: increase; ↓: decrease; ↑↑↑:prominent increase; +: presence; −: absence; ~: similar to the wild type; na: not analyzed In FIG. 10A, HE staining was used to analyze the coronal sections of the lumbar spinal cords of 6-month old wild type (WT) and TDP-43 Tg(+/+) mice. The scale bars are 100 μm. The upper 2 panels show the representative spinal cords at single anatomical level, each one for the WT and Tg(+/+) mice. The lower panels are magnified pictures of the inserts in the upper two panels. Note the similarity of the staining patterns between the WT and Tg(+/+) mice. Results are representative of three independent experiments. FIG. 10B shows bar graphs of the numbers of motor neurons per lumbar spinal cord section of the WT and TDP-43 Tg(+/+) mice. The criteria for selecting the scored motor neurons included their having a round/open/pale nucleus with the diameter of 30-45 μm. For each animal, more than 25 coronal sections from L1 to L5 of the lumbar spinal cord were counted. The numbers of the spinal motor neurons (MN) are similar between the WT and TDP-43 Tg(+/+) mice ($p>0.05$). Results represent the mean±SEM of three independent experiments and N is 5 for each group.

Figure 3:
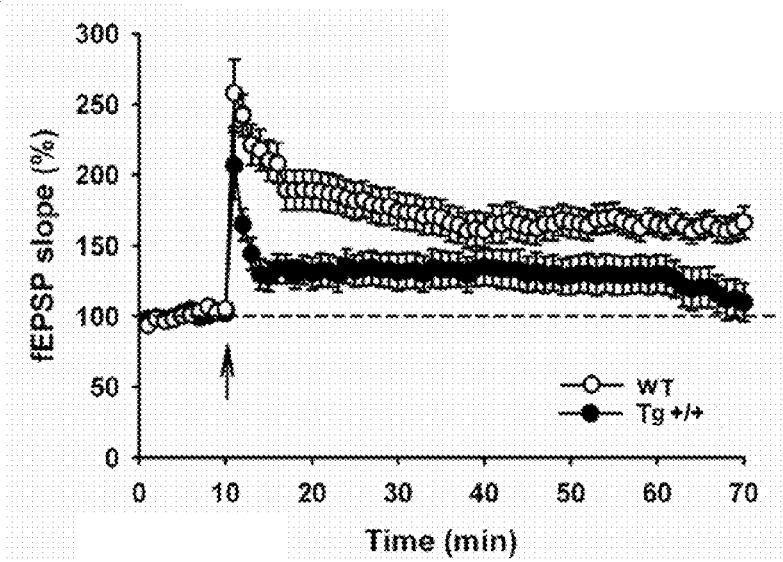
FIGS. 3A-3B show the results of the electrophysiology study of the CaMKII-TDP-43 Tg mice.
Figure 3:
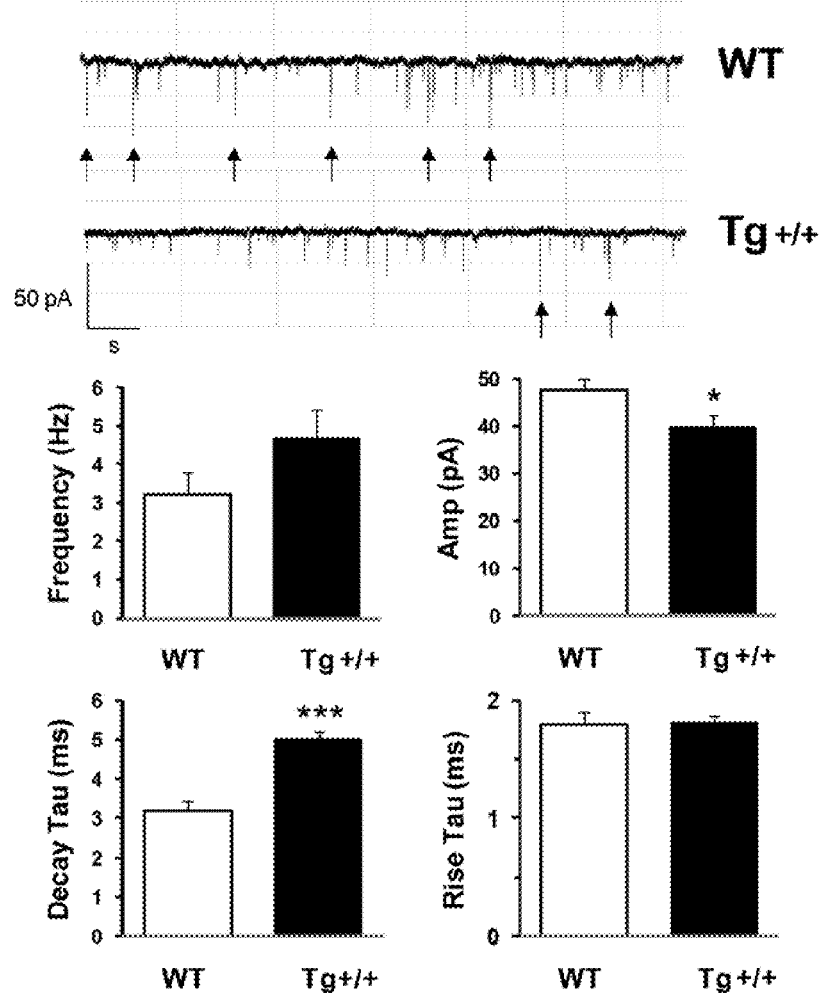

The CaMKII-TDP-43 Tg mice also exhibited cognitive impairments as reflected by the Morris water maze test (FIG. 2A), fear conditioning task (FIG. 2B), novel object recognition test (FIG. 2F), and LTP electrophysiological recording (FIG. 3). Related to this, the learning/memory deficiency in the FTLD patients is the major factor leading to the dysfunctions of their social behavior and language. As a preliminary investigation of the molecular and cellular basis of the effect of the overexpressed TDP-43 on the cognitive functions, we have examined the expression levels of several molecular markers of neuronal plasticity. The results (FIG. 4) indicated that overexpression of TDP-43 has led to decreases in both p-ERK and p-CREB (FIG. 4), and likely their downstream targets such as BDNF, etc. (Kandel, 2001). Furthermore, the enhanced gliosis, as observed in the Tg mice (FIG. 5A), is also known to impair learning/memory. Since overexpression of TDP-43 affects a range of biological activities in cell cultures, e.g., transcription, alternative splicing, cell cycle progression, etc., it is expected that the phenotypes of the Tg mice resulted from alternations/modifications of multiple biological processes as mis-regulated by the overexpressed TDP-43 in the cortex and hippocampus. It should be noted here that one of our previous studies has shown that TDP-43 is distributed in the dendrites of cultured hippocampal neurons as granules/RNA granules. However, we have detected no apparent difference in either the distribution pattern or the number of the TDP-43 granules between cultured hippocampal neurons prepared from Tg and WT mice (data not shown).

Figure 5:
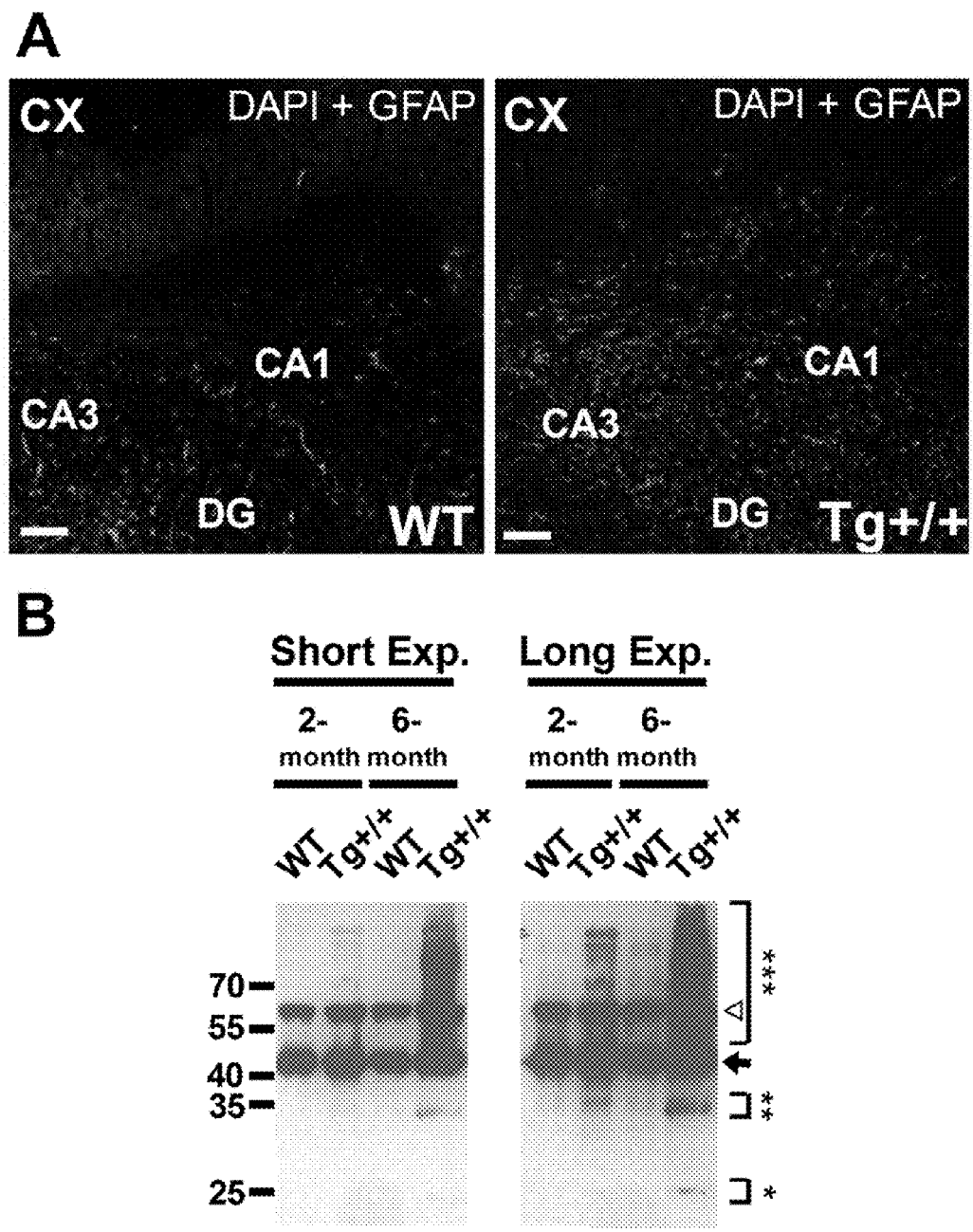
FIGS. 5A-5B show neurodegeneration of the brains of CaMKII-TDP-43 Tg mice.
Figure 6:
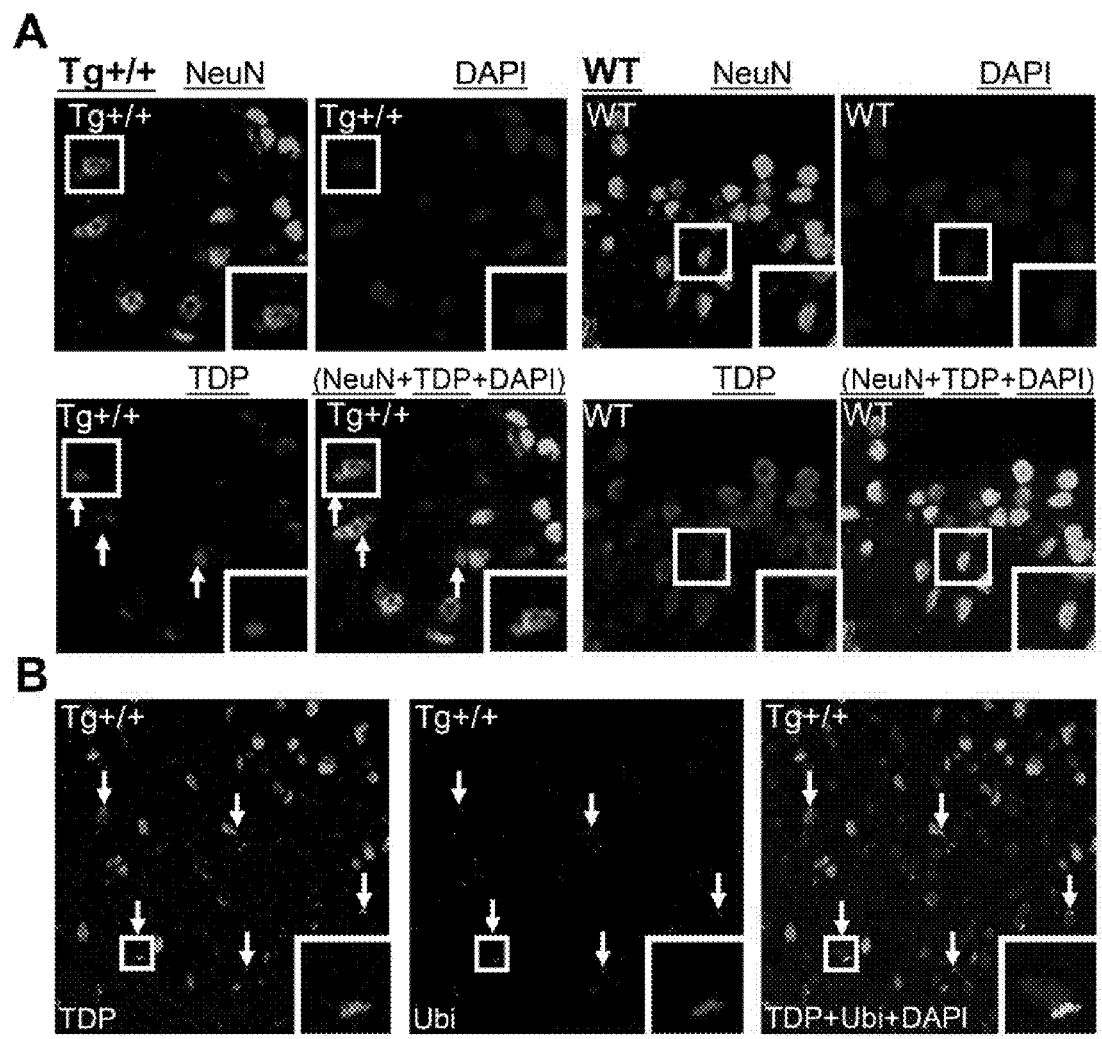
FIGS. 6A-6B show immunofluorescence staining analysis of TDP-43 distribution in the neurons of the mouse brains.

In addition to the behavioral phenotypes, the TDP-43 Tg mice also exhibited patterns of neuropathology similar to those of FTLD-U except for the apparent absence of the phosphorylated 45 kDa TDP-43 (FIG. 5). Specifically, neurons with TDP-43 depleted nuclei and cytoplasmic TDP-43 (+), ubiquitin(+) inclusions (UBIs) were present in brain sections of the 6-month old Tg mice, although they could not be detected in the 2-month old Tg mice (FIGS. 6A, 6B, and Table 1). This age-dependent pattern of immunohistochemistry analysis was in good correlation with the immunoblotting data showing the enrichment of the high molecular weight TDP-43 species, presumably the poly-ubiquitinated TDP-43, and the 25 kDa as well as 35 kDa TDP-43 fragments in the urea-soluble fractions of the brain extracts from 6-month-old Tg mice (FIG. 5B and Table 1). Thus, it seemed that the appearance of the insoluble TDP-43(+) UBIs was a priori for the loss of the motor functions but not the cognitive functions in the mouse model. On the other hand, the appearance of the NCIs could just be a secondary, age-dependent phenomenon and that some other still un-identified process(es) was responsible for the motor dysfunction of the 6-month-old Tg mice. The basis for this differential correlation and whether it exists during the development of the human FTLD-U cases await to be investigated.

Overall, it has been demonstrated that transgenic overexpression of TDP-43 in the forebrains of mice leads to development of molecular, cellular, behavioral, and proteinopathological characteristics similar to those identified in FTLD-U. Significantly, there are FTLD-MND patients whose brain TDP-43 mRNA levels are higher than the normal controls. A global gene expression study has also found higher level of TDP-43 mRNA in several cases of PGRN-mutation positive FTLD-U. Notably, immunoblotting analysis of lysates from some of ALS pathological samples as well as myopathy muscles with TDP-43(+) inclusions has also revealed higher TDP-43 protein levels than the normal controls. Thus, our data on the CaMKII-TDP-43 Tg mice suggest that the elevation of the level of TDP-43 protein could be one of the primary causes leading to the pathogenesis of neurodegenerative diseases with TDP-43(+) inclusions.

It is interesting to compare a few aspects of this study with that by Wils et al. (2010). Firstly, the data from the two studies together provide a strong support for the notion that elevated level of TDP-43 suffices the induction of neurodegeneration in mice, and very likely it is also responsible for the generation and development of the neurodegenerative diseases with TDP-43 proteinopathies in humans. Secondly, both studies have identified TDP-43-cotaining NCIs as well as activation of caspase-3 in association with neuronal apoptosis. Thirdly, both studies have detected the appearances of the 35 KDa and 25 KDa C-terminal fragments of TDP-43 along the course of the pathogenesis development. Finally, Wils et al. (2010) utilized the Thy-1 promoter to direct the TDP-43 overexpression in the mice, which is active in a wider range of different types of cells including neurons of the central nervous system, the muscle cells, the immune T-cells, etc. They characterized mainly the motor neuron dysfunction- and muscle defect-related pathology and behavioral phenotypes of the transgenic mice, such as the spastic paralysis, muscle wasting, reduced movement, etc. On the other hand, use of the forebrain neuron-specific CaMKII promoter in the present invention has allowed the detection and follow-up of pathogenesis development of cognitive behaviors as well as the motor function of mice from youth to the age of over 2 years. In addition, several hallmarks of FTLD-U, including cognitive dysfunction, hippocampal atrophy, and progressive appearances of 35 KDa and 25 KDa fragments as well as high molecular weight species of TDP-43 in the urea-soluble fraction of the disease forebrains (Table 1) could be observed in these mice. Thus, while the mice generated by Wils et al. (2010) are more suitable for studies of neurodegeneration reminiscent of ALS, the CaMKII-TDP-43 Tg mice according to the invention are ideal for future detailed pathological/clinical analysis and drug/therapeutic development for FTLD-U.

All of the references cited herein are incorporated by reference in their entirety.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

LIST OF REFERENCES

Cao, X., H. Wang, B. Mei, S. An, L. Yin, L. P. Wang, and J. Z. Tsien. 2008. Inducible and selective erasure of memories in the mouse brain via chemical-genetic manipulation. *Neuron.* 60:353-66.

Nara, T., K. Nakamura, M. Matsui, A. Yamamoto, Y. Nakahara, R. Suzuki-Migishima, M. Yokoyama, K. Mishima, I. Saito, H. Okano, and N. Mizushima. 2006. Suppression of basal autophagy in neural cells causes neurodegenerative disease in mice. *Nature.* 441:885-9.

Mayford, M., M. E. Bach, Y. Y. Huang, L. Wang, R. D. Hawkins, and E. R. Kandel. 1996. Control of memory formation through regulated expression of a CaMKII transgene. *Science.* 274:1678-83.

Neumann, M., D. M. Sampathu, L. K. Kwong, A. C. Truax, M. C. Micsenyi, T. T. Chou, J. Bruce, T. Schuck, M. Grossman, C. M. Clark, L. F. McCluskey, B. L. Miller, E. Masliah, I. R. Mackenzie, H. Feldman, W. Feiden, H. A. Kretzschmar, J. Q. Trojanowski, and V. M. Lee. 2006. Ubiquitinated TDP-43 in frontotemporal lobar degeneration and amyotrophic lateral sclerosis. *Science.* 314:130-3.

Tsai, K. J., Y. C. Tsai, and C. K. J. Shen. 2007. G-CSF rescues the memory impairment of animal models of Alzheimer's disease. *J Exp Med.* 204:1273-80.

Wang, I. F., L. S. Wu, H. Y. Chang, and C. K. J. Shen. 2008b. TDP-43, the signature protein of FTLD-U, is a neuronal activity-responsive factor. *J Neurochem.* 105:797-806.

Wils, H., G. Kleinberger, J. Janssens, S. Pereson, G. Doris, I. Cuijt, V. Smits, C. C. Groote, C. Van Broeckhoven, and S. Kumar-Singh. TDP-43 transgenic mice develop spastic paralysis and neuronal inclusions characteristic of ALS and frontotemporal lobar degeneration. *Proc Natl Acad Sci USA.*

Winton, M. J., L. M. Igaz, M. M. Wong, L. K. Kwong, J. Q. Trojanowski, and V. M. Lee. 2008. Disturbance of nuclear and cytoplasmic TAR DNA-binding protein (TDP-43) induces disease-like redistribution, sequestration, and aggregate formation. *J. Biol Chem.* 283:13302-9.

What is claimed is:

1. A transgenic mouse whose genome comprises a transgene operably linked to a $Ca^{2+}$/calmodulin-dependent kinaseIIα (CaMKIIα) promoter effective for an increased expression of the transgene in the brain of the mouse, the transgene comprising a nucleotide sequence encoding TAR DNA-binding protein 43 (TDP-43), wherein the mouse exhibits an increased expression of TDP-43 in the brain thereof.

2. The transgenic mouse of claim 1, wherein the mouse exhibits reduced or impaired learning and memory capacity.

3. The transgenic mouse of claim 2, wherein the mouse further exhibits progressively impaired or reduced motor functions.

4. The transgenic mouse of claim 1, whose hippocampus and cortex, but not cerebellum and spinal cord, exhibit an increased amount of TDP-43 protein.

5. The transgenic mouse of claim 4, which is either a homozygous or hemizygous transgenic mouse, wherein the homozygous mouse and hemizygous transgenic mouse exhibit similar levels of TDP-43 protein.

6. The transgenic mouse of claim 1, whose hippocampus and cortex, but not cerebellum and spinal cord, exhibit at least a 2-fold increase in the level of TDP-43 protein.

7. The transgenic mouse of claim 1, whose hippocampus and cortex exhibit an altered level of a protein and/or a neurotransmitter member selected from the group consisting of phosphorylated extracellular signal-regulated kinase (pERK), phosphorylated cAMP-response element-binding Protein (pCREB), glutamic acid decarboxylase 67 (GAD67), glial fibrillary acidic protein (GFAP), gamma-aminobutyric acid (GABA) and capsase-3.

8. The transgenic mouse of claim 1, wherein the brain of the mouse exhibits poly-ubiquitinated TDP-43.

9. The transgenic mouse of claim 8, wherein the amount of poly-ubiquitinated TDP-43 in the brain of the mouse increases with age.

10. The transgenic mouse of claim 1, wherein the brain neurons of the mouse exhibits cytoplasmic TDP-43 inclusion bodies.

11. The transgenic mouse of claim 10, wherein the cytoplasmic TDP-43 inclusion bodies are ubiquitin positive.

12. The transgenic mouse of claim 1, wherein the mouse exhibits brain atrophy, neuronal loss and learning memory loss.

13. A method for evaluating potential therapeutic effects of a compound for treating, preventing and/or inhibiting frontotemporal lobar degeneration with ubiquitin-positive inclusions (FTLD-U) in a mammal, comprising the steps of:
  (a) administering the compound to a transgenic mouse according to claim 1; and
  (b) determining the potential therapeutic effects of the compound on the transgenic mouse by indentifying improvement in learning and memory behavior and/or motor function of the tansgeinc mouse.

14. A method for identifying a candidate agent for treating, preventing and/or inhibiting FTLD-U, comprising the steps of:
  a) measuring the level of TDP-43 expression in the transgenic mouse of claim 1;
  b) administering the agent to the transgenic mouse; and
  c) measuring the level of TDP-43 expression in the transgenic mouse;
  wherein a decrease in the level of TDP-43 expression after treatment with the agent identifies the agent as a candidate agent for treating, preventing and/or inhibiting FTLD-U.

15. A neuronal cell isolated or derived from a transgenic mouse according to Claim 1, the neuronal cell expressing an increased level of TDP-43-mRNA as compared to a neuronal cell isolated or derived from a non-transgenic mouse.

16. The neuronal cell of claim 15, wherein the neuronal cell exhibits TDP-43 protein inclusion bodies in the cytosol thereof.

17. A neuronal cell comprising a transgene operably linked to a $Ca^{2+}$/calmodulin-dependent kinaseIIα (CaMKIIα)promoter effective for an increased expression of the transgene in the neuronal cell, the transgene comprising a nucleotide sequence encoding TAR DNA-binding protein 43 (TDP-43), wherein the neuronal cell exhibits TDP-43 protein inclusion bodies in the cytosol thereof.

18. The neuronal cell of claim 17, wherein the neuronal cell exhibits TDP-43 protein inclusion bodies in the cytosol thereof.

* * * * *